(12) United States Patent
Samant et al.

(10) Patent No.: US 11,464,470 B2
(45) Date of Patent: Oct. 11, 2022

(54) X-RAY BACKSCATTER SYSTEMS AND METHODS FOR PERFORMING IMAGING TOMOSYNTHESIS

(71) Applicant: University of Florida Research Foundation, Inc., Gainesville, FL (US)

(72) Inventors: Sanjiv Singh Samant, Gainesville, FL (US); Lucas M. Rolison, Los Alamos, NM (US); James Edward Baciak, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 17/046,479

(22) PCT Filed: Apr. 11, 2019

(86) PCT No.: PCT/US2019/027103
§ 371 (c)(1),
(2) Date: Oct. 9, 2020

(87) PCT Pub. No.: WO2019/200180
PCT Pub. Date: Oct. 17, 2019

(65) Prior Publication Data
US 2021/0030383 A1    Feb. 4, 2021

Related U.S. Application Data

(60) Provisional application No. 62/656,117, filed on Apr. 11, 2018.

(51) Int. Cl.
*A61B 6/00* (2006.01)
*A61B 6/02* (2006.01)
*A61B 6/03* (2006.01)

(52) U.S. Cl.
CPC .............. *A61B 6/483* (2013.01); *A61B 6/025* (2013.01); *A61B 6/032* (2013.01); *A61B 6/4078* (2013.01); *A61B 6/466* (2013.01); *A61B 6/5205* (2013.01)

(58) Field of Classification Search
CPC ......... A61B 6/032; A61B 6/5282; A61B 6/06; A61B 6/483; A61B 6/025; A61B 6/4078;
(Continued)

(56) References Cited

U.S. PATENT DOCUMENTS

| 5,600,700 A | 2/1997 | Krug |
| 6,252,929 B1 | 6/2001 | Swift |

(Continued)

FOREIGN PATENT DOCUMENTS

EP    2743687 A1    6/2014

OTHER PUBLICATIONS

International Search Report and Written Opinion dated Jul. 16, 2019 in co-pending PCT Application No. PCT/2019/027103.
(Continued)

*Primary Examiner* — Courtney D Thomas
(74) *Attorney, Agent, or Firm* — Thomas | Horstemeyer, LLP

(57) ABSTRACT

X-ray backscatter imaging (XBI) methods and systems are provided that enable depth-sensitive information to be obtained from images acquired during a single scan from a single side of an object being imaged. The depth-sensitive information is used in combination with other image information acquired during the scan to produce high-resolution 2-D or 3-D images, where at least one of the dimensions of the 2-D or 3-D image corresponds to depth in the object.

20 Claims, 27 Drawing Sheets

(58) Field of Classification Search
CPC .... A61B 6/466; A61B 6/5205; G01N 23/046; G01N 23/203; G01V 5/0025; G06T 2211/436; G06T 11/006
See application file for complete search history.

(56) References Cited

U.S. PATENT DOCUMENTS

| | | | |
|---|---|---|---|
| RE39,396 E | | 11/2006 | Swift |
| 7,649,976 B2* | | 1/2010 | Georgeson ............ G01N 23/203 378/57 |
| 9,036,781 B1 | | 5/2015 | Safai |
| 9,846,258 B2 | | 12/2017 | Chen |
| 2007/0206726 A1 | | 9/2007 | Lu et al. |
| 2008/0253511 A1 | | 10/2008 | Boyden et al. |
| 2012/0123697 A1 | | 5/2012 | Fabiani et al. |
| 2012/0144102 A1 | | 5/2012 | Chapman et al. |
| 2013/0206985 A1* | | 8/2013 | Turner ............. G01N 23/20066 250/310 |
| 2014/0247920 A1 | | 9/2014 | Marks et al. |
| 2016/0003954 A1 | | 1/2016 | Broussard |
| 2018/0017685 A1 | | 1/2018 | Cao |

OTHER PUBLICATIONS

Burke, et al., "NDE of spacecraft materials using 3D compton backscatter x-ray imaging", 42nd annual review of progress in quantitative nondestructive evaluation, AIP Publishing 2016.
Grubsky, et al., "Recent progress on 3D backscatter x-ray NDE", Physical Optics Corporation, Jul. 15, 2014.
Harding, et al. "Compton scatter imaging: A tool for historical exploration", Applied Radiation and Isotopes 68 (2010).
Rolison, et al., "Proof of concept for X-ray backscatter Imaging tomosynthesis using spectral detection", IEEE 2017.
Rolison, et al., "Proof of concept for X-ray backscatter Imaging tomosynthesis using spectral detection", Poster US Department of Energy, 2017.

* cited by examiner

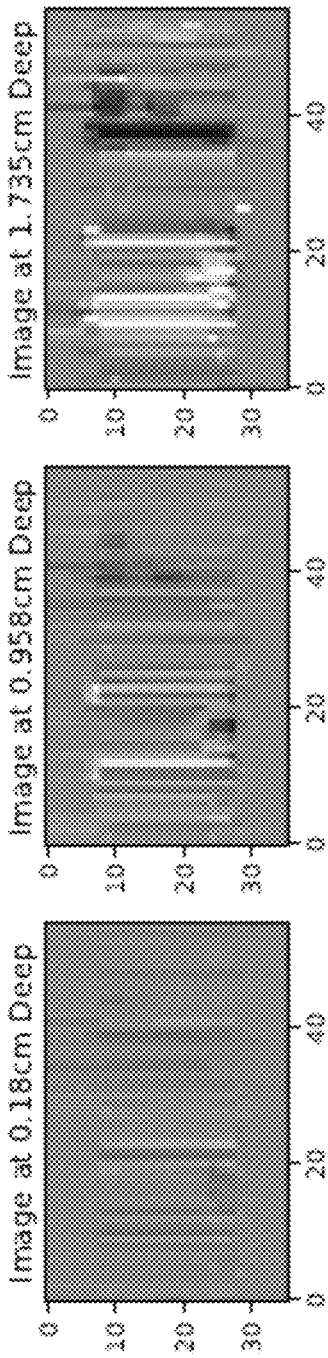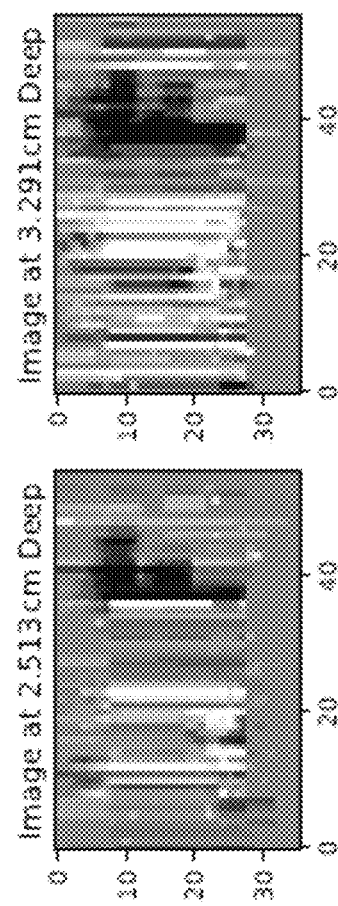
FIG. 21A FIG. 21B FIG. 21C FIG. 21D FIG. 21E

4 Projections

3 Projections

1 Projection

64 Projections

32 Projections

16 Projections

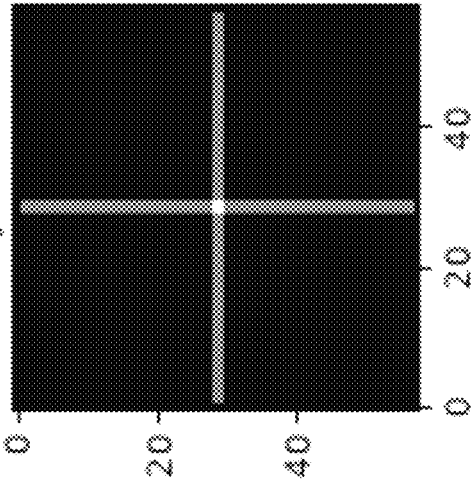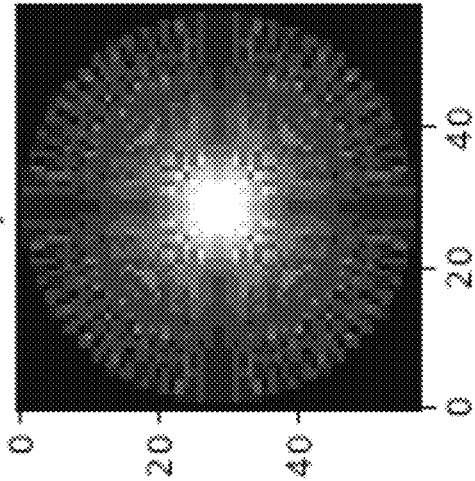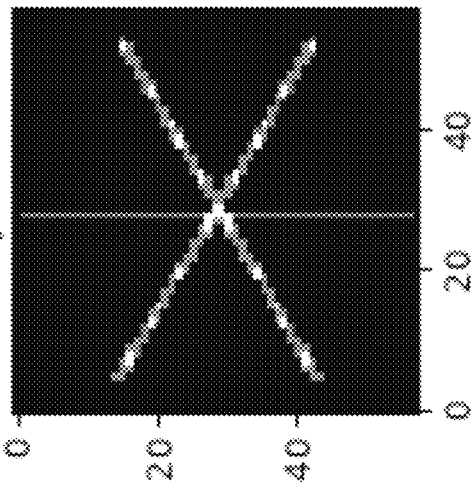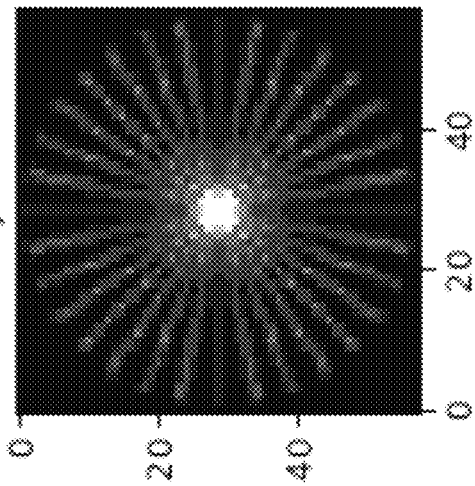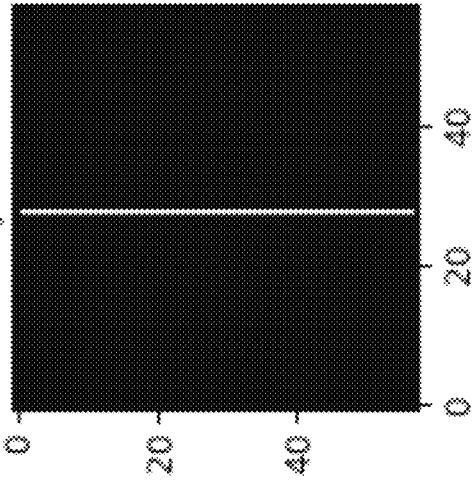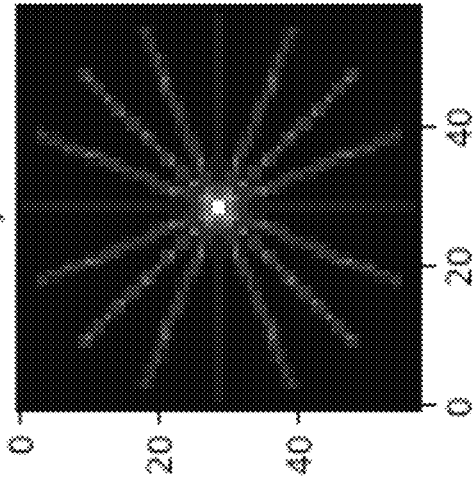

Image at 1.735cm Deep

Image at 0.958cm Deep

Image at 0.18cm Deep

Image at 3.291cm Deep

Image at 2.513cm Deep

Image at 1.735cm Deep

Image at 0.958cm Deep

Image at 3.291cm Deep

Image at 0.18cm Deep

Image at 2.513cm Deep

X-RAY BACKSCATTER SYSTEMS AND METHODS FOR PERFORMING IMAGING TOMOSYNTHESIS

CROSS-REFERENCE TO RELATED APPLICATIONS

The present application is being filed under 35 U.S.C. § 371 as a U.S. National Phase Application of PCT International Application No. PCT/CN2019/027103 filed on Apr. 11, 2019, entitled "X-RAY BACKSCATTER SYSTEMS AND METHODS FOR PERFORMING IMAGING TOMOSYNTHESIS," which claims the benefit of and priority to the filing date of U.S. provisional application Ser. No. 62/656,117, filed on Apr. 11, 2018 and entitled "X-RAY BACKSCATTER SYSTEMS AND METHODS FOR PERFORMING IMAGING TOMOSYNTHESIS," both of which are hereby incorporated by reference herein in their entireties.

BACKGROUND

X-ray backscatter systems create images of the internal structure of objects while both X-ray source and detectors are placed on the same side of the object. One sided imaging is useful when the object being imaged is either too voluminous or access to its opposite side is impossible or impractical. However, existing X-ray backscatter designs typically acquire only two-dimensional (2-D) images and previous attempts to go beyond that involve obtaining multiple scans.

Compton scatter imaging (CSI) is a technique similar to that of transmission radiography except that it utilizes the inelastic scattering of photons to acquire spatial information about the object under investigation. Since photons scatter in all directions, it is possible to place photon detectors in a CSI system at locations that would otherwise be impossible for a transmission imaging system to use (detectors of transmission imaging systems must be in line with the primary beam path and on the opposite side of the object).

X-ray backscatter imaging (XBI) can be considered a subset of CSI, where X-rays are the photon source and the detectors are placed on the same side of the object as the X-ray source. This constitutes a design that collects X-rays scattering at angles greater than 90° and only needs access to one side of the object being imaged. XBI has useful applications in non-destructive testing and the potential for use in medical imaging, where the object being imaged is either too voluminous or access to its opposite side is impossible or impractical. Although it is possible to achieve tomographic imaging with CSI designs, they almost always place detectors on the far side of the object from the photon source and sometimes use the additional information from transmission images. This means very little work has been achieved in XBI in regards to tomography, which is a method of producing 2-D and three-dimensional (3-D) images of internal structures of an object. The primary reason for this is because of how limiting signal acquisition is when performed from only a single side of the object.

A need exists for a method and system for using XBI to obtain 2-D and 3-D images that include depth-sensitive information. A need also exists for a method and system for using XBI to obtain such images at relatively low radiation dose levels and with relatively short image acquisition times.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIGS. 21A-21E show the resulting 3-D images acquired by a 2-D XBI system simulated in MCNP6. Noise in image is due to limitations in the run time of Monte Carlo simulations/computations, and is not due to inherent issues in the XBI system.

FIGS. 23 and 24 show images that demonstrate an uneven distribution of sampling for a top/surface of a voxel map and the bottom/deepest of the map, respectively, when a fan-shaped beam is used.

DETAILED DESCRIPTION

Figure 1:
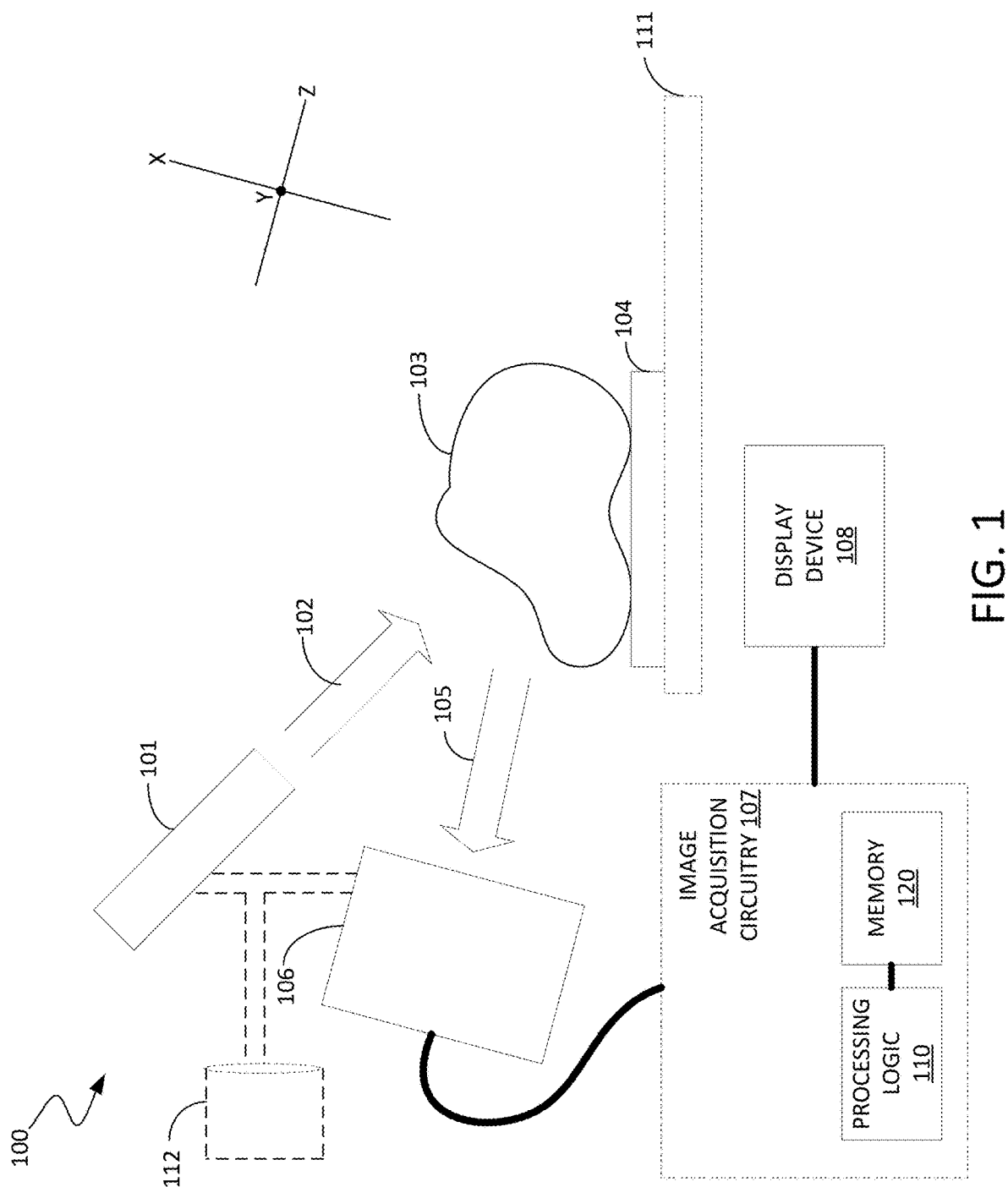
FIG. 1 illustrates a block diagram of an XBI system in accordance with a representative embodiment that is capable of producing 2-D and 3-D images that include depth-sensitive information during a single scan.

The inventive principles and concepts are directed to XBI methods and systems that acquire depth-sensitive information during a single scan that is used in combination with other information acquired during the scan to produce 2-D and 3-D images. The XBI system can have a variety of system configurations. Likewise, various XBI methods can be used. The following describes examples of a few XBI system configurations and examples of various XBI methods that can be used with the system configurations.

In the following detailed description, for purposes of explanation and not limitation, example embodiments disclosing specific details are set forth in order to provide a thorough understanding of an embodiment according to the present teachings. However, it will be apparent to one having ordinary skill in the art having the benefit of the present disclosure that other embodiments according to the present teachings that depart from the specific details disclosed herein remain within the scope of the appended claims. Moreover, descriptions of well-known apparatuses and methods may be omitted so as to not obscure the description of the example embodiments. Such methods and apparatuses are clearly within the scope of the present teachings.

The terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms "a," "an," and "the" include both singular and plural referents, unless the context clearly dictates otherwise. Thus, for example, "a device" includes one device and plural devices.

Relative terms may be used to describe the various elements' relationships to one another, as illustrated in the accompanying drawings. These relative terms are intended to encompass different orientations of the device and/or elements in addition to the orientation depicted in the drawings.

It will be understood that when an element is referred to as being "connected to" or "coupled to" or "electrically coupled to" another element, it can be directly connected or coupled, or intervening elements may be present.

The term "memory" or "memory device", as those terms are used herein, are intended to denote a computer-readable storage medium that is capable of storing computer instructions, or computer code, for execution by one or more processors. References herein to "memory" or "memory device" should be interpreted as one or more memories or memory devices. The memory may, for example, be multiple memories within the same computer system. The memory may also be multiple memories distributed amongst multiple computer systems or computing devices.

A "processor", as that term is used herein encompasses an electronic component that is able to execute a computer program or executable computer instructions. References herein to a computer comprising "a processor" should be interpreted as a computer having one or more processors or processing cores. The processor may for instance be a multi-core processor. A processor may also refer to a collection of processors within a single computer system or distributed amongst multiple computer systems. The term "computer" should also be interpreted as possibly referring to a collection or network of computers or computing devices, each comprising a processor or processors. Instructions of a computer program can be performed by multiple processors that may be within the same computer or that may be distributed across multiple computers.

Exemplary, or representative, embodiments will now be described with reference to the figures, in which like reference numerals represent like components, elements or features. It should be noted that features, elements or components in the figures are not intended to be drawn to scale, emphasis being placed instead on demonstrating inventive principles and concepts.

FIG. 1 illustrates an XBI system 100 in accordance with a representative embodiment that is capable of producing 2-D and 3-D images that include depth-sensitive information during a single scan. An X-Ray source 101 of the XBI system 100 emits X-Rays 102 toward an object 103 being imaged, which is supported on a support structure 104. X-Ray photons 105 backscattered by the object 103 are received by an X-Ray detector array 106. The X-Ray detector array 106 of the XBI system 100 has an array of X-Ray detectors that detect the backscattered X-Ray photons and output respective electrical signals. It should be noted that the X-Ray source 101 and the X-Ray detector array 106 are positioned on the same side of the object 103, which is referred to herein as the first side of the object 103.

Image acquisition circuitry 107 of the XBI system 100 acquires the electrical signals output by the X-Ray detectors of the array 106 during a single scan and generates at least one of a 2-D or a 3-D image that includes depth-sensitive information. At least one of the dimensions of the 2-D or 3-D image corresponds to depth-sensitive information. For example, if the rows and columns of the X-Ray detector array 106 are parallel to X- and Y-axes, respectively, of the X, Y, Z Cartesian Coordinate system shown in FIG. 1, depth inside of the object 103 corresponds to a direction that is parallel to the Z-axis of the X, Y, Z Cartesian Coordinate system. The 2-D or 3-D image generated by the image acquisition circuitry 107 is typically displayed on an optional display device 108 of the XBI system 100.

The image acquisition circuitry 107 typically includes processing logic 110 and a memory device 120. The processing logic 110 comprises one or more processors that perform one or more algorithms that process the image data acquired by the image acquisition circuitry 107 to generate the 2-D or 3-D tomographic images. The algorithm(s) will depend on the method that is being implemented by the XBI system 100. Examples of the algorithm are discussed below in more detail.

As will be discussed below in more detail, in some embodiments, the XBI system 100 includes a rotational translating system 111 that rotates the support structure 104, thereby rotating the object 103, as the X-Ray source 101 and the X-Ray detector array 106 remain stationary. In some embodiments, the XBI system 100 includes a rotational translating system 112 that rotates the X-Ray source 101 and the X-Ray detector array 106 together relative to a fixed point on the object 103 as the object 103 remains stationary.

In accordance with an embodiment, the processing logic 110 performs a binning algorithm. In accordance with this embodiment, the X-Ray source 101 and the X-Ray detector array 106 can have virtually any geometries. The binning algorithm uses N energy levels as N threshold (TH) values, respectively, and compares each respective energy level of each of the acquired electrical signals to the N TH values, where N is a positive integer that is greater than or equal to one. The processing logic 110 allocates a digital representation of each respective acquired electrical signal to one of N+1 bins in the memory 120 based on the results of the comparison. The processing logic 110 generates the depth-sensitive information based, at least in part, on which of the bins each of the acquired electrical signals has been allocated to the memory 120. As an alternative to using TH values, one could instead use energy intervals, which is possible with today's detectors in tandem with multichannel analyzers.

For the embodiment that uses the binning algorithm, they are several choices for the geometries for the X-Ray source 101 and the X-Ray detector array 106. For example, the X-Ray source 101 may be configured to generate a single generally pencil-shaped beam of X-Ray radiation and the X-Ray detector array 106 may have a single collimated or non-collimated X-Ray detector (i.e., a 1×1 array). As another example, the X-Ray source 101 may be configured to generate a generally fan-shaped beam of X-Ray radiation and the X-Ray detector array 106 may have a 2-D array of collimated X-Ray detectors. As yet another example, the X-Ray source 101 may be configured to generate a line array of generally pencil-shaped beams of X-Ray radiation and the X-Ray detector array 106 may have a 2-D array of collimated X-Ray detectors.

In accordance with another embodiment, the depth-sensitive information is obtained by using a 2-D X-Ray detector array 106 and ensuring that each row of the detectors views a different depth inside of the object 103. In accordance with this embodiment, the X-Ray detector array comprises an array of X rows and Y columns, where X and Y are integers that are greater than or equal to 2. The X rows and Y columns are parallel to the X- and Y-axes, respectively, of the X, Y, Z Cartesian coordinate system. Each of the X rows of the X-Ray detectors points toward a different depth in the object, where the depth in the object corresponds to a direction that is parallel to the Z-axis of the X, Y, Z Cartesian coordinate system. Each of the X-Ray detectors is collimated. The depth-sensitive information is generated based on where each row in the 2-D X-Ray detector 106 is pointed at inside the object being imaged.

In accordance with this embodiment in which each row of detectors views a different depth inside of the object 103, the XBI system 100 can have a variety of configurations. For example, the X-Ray source 101 may be configured to generate a generally fan-shaped beam of X-Ray radiation and the X-Ray detector array 106 is offset from the generally fan-shaped beam and angled such that a front face of the X-Ray detector array 106 is pointing toward the first side of the object 103, as shown in FIG. 1. Alternatively, the X-Ray source 101 may be configured to generate a line array of generally pencil-shaped beams of X-Ray radiation. With any of these system configurations, the rotational translating system 112 may be used to rotate the X-Ray source 101 and the X-Ray detector array 106 together relative to a fixed point on the object 103 as the object 103 remains stationary. During the rotation, a single scan is acquired by the image acquisition circuitry 107. The processing logic 110 then performs a back projection algorithm that processes digital representations of the electrical signals output from the detectors at different angles of the rotating X-Ray source 101 and X-Ray detector array 106 to reconstruct a 3-D image of the object 103 that includes depth-sensitive information or a 3-D slice or cross-section of the object 103 that includes depth-sensitive information.

In accordance with this embodiment in which each row of detectors views a different depth inside of the object 103, the X-Ray source 101 and the X-Ray detector array 106 may be held stationary as the rotational translating system 111 is used to rotate the object 103 as the X-Ray source 101 and the X-Ray detector array 106 remain stationary. The processing logic 110 then performs a back projection algorithm that processes digital representations of the electrical signals output from the detectors at different angles of the rotating object 103 to reconstruct a 3-D image of the object 103 or a 3-D image of a slice or cross-section of the object 103 that includes depth-sensitive information.

Having described various examples of XBI system configurations and methods, a detailed description of experiments that were conducted and simulated will now be provided.

Experiments and Computer Simulations

Computer simulations have become an effective way to conduct science that would otherwise be cost prohibitive or impractical if they were to be physically implemented. This especially holds true for nuclear science and engineering, where equipment and resources can be quite expensive, even before the cost of safety measures are taken into account. However, the accuracy of computer simulations are only as reliable as the data that it is put into it. In this case data are referring to: the algorithms used to model the physics; the physical, experimental data (temperature, nuclear cross-sections, etc.); and the information provided by the user. Therefore it is important that verification and validation studies are performed on computer codes in order to improve the trustworthiness of the results they provide.

For these reasons, the radiation transport code Monte Carlo N-Particle (MCNP)6 was used to model XBI systems in order to assess their capabilities and test the new 3-D imaging techniques. MCNP was chosen because it is a well established code, with extensive verification and validation performed on its physics modeling and up-to-date nuclear cross-section data. MCNP6 is the latest version in the long history of MCNP, offering new capabilities that were not available before. Examples of new capabilities include (but are not limited to): improved physics modeling, new source modeling capabilities, and mesh tally improvements. One improvement that is of particular interest is "enhanced photon form factors", which provides the code with a more complete representation of photon scattering.

Since MCNP6 is a stochastic code, a major concern was achieving accurate results with low uncertainty. This means that certain problems can require long runtimes—hours or even days—depending on the desired results of the simulation. MCNP6 is extremely parallelizable, which means many processors can be used to run a single simulation, thereby reducing runtime. For this XBI experimental work, the use of the University of Florida's (UF) high performance computing (HPC) cluster was essential. As will be discussed in the next section, a vast number of simulations and processors were used in order to achieve results within a reasonable time frame.

XBI is not a common use for MCNP6, so there are no proper validation studies that have been conducted for it. Therefore it was important to first perform a validation study, albeit a crude one, on previous XBI works before moving forward with new imaging techniques. The test cases discussed herein offer a more qualitative rather than quantitative analysis of XBI in MCNP6.

The primary reason for this is the lack of information about older studies. Since almost all XBI systems are prototypes, there was missing information about the physical dimensions. Such dimensions include the distance between X-ray source and radiation detectors and the distance between the system and the surface of the object being scanned. Another piece of valuable information missing was the energy spectra of the X-ray tubes being used. All of this information has a great influence on the kind of signal an XBI system would acquire. Furthermore, photon counts are not provided for each pixel in the images presented in these studies, so there was no definitive way to validate MCNP's results to that of the experiments.

The main focus on these validation tests were to determine whether simulated images show similar color contrasts to that of the real images, as well as test the depth discrimination abilities of XBI proven in a paper by B. C. Towe and A. M. Jacobs, entitled "X-Ray backscatter Imaging," published IEEE Trans. Biomed. Eng., vol. BME-28, no. 9, pp. 646-654, September 1981 (hereinafter "Towe and Jacobs").

For both validation tests, the XBI systems used were based on a point-by-point scanning method utilizing an X-Ray source configured to emit a generally pencil beam-shaped X-ray source and common, cylindrical detectors. The XY plane is parallel to the surface of the object being imaged while the Z dimension represents the depth dimension going into the object. Therefore a pencil-beam XBI system will raster scan in the XY dimensions over the object surface. Each pixel in the resulting image refers to a point the system stopped at and collected scattered X-rays with its detectors. The number of detectors used in a design such as this does not increase the number of pixels measured at one scan step, it only improves the count rate (reduced scan times) and removes streaking artifacts due to measuring scattered X-rays from a single angle. Streaking artifacts will be discussed below in further detail.

A generally pencil-shaped beam was formed in MCNP6 by biasing a point source so that it projected a cone of photons towards the phantom. Then by placing a cell of importance 0 with a square whole in front of the cone, the cone beam is shaped into a square pencil beam of a desired size. Since photons are killed and no longer tracked in MCNP when they pass through a cell of importance 0, this system is an ideal pencil-beam of radiation with no photons leaking out towards the detectors. It's as if the X-ray tube is perfectly collimated so that only X-rays can come from the pencil-beam. This can be easily achieved in a real system as well by shielding both the X-ray tube and detectors so that no leakage photons add erroneous signal to the detectors.

Since a generally pencil-shaped beam goes point-by-point, there must be a separate MCNP6 simulation for each pixel imaged, since the system is physically moving each time. This means hundreds of processors are being used at once, with at least one dedicated to each simulation scan point. Python scripts were written to aid in the rapid duplication and editing of MCNP6 input files in order to simulate this system scanning method. This process is simplified by the transformation (TR) card available in MCNP6. This allows the objects assigned to the TR card to be shifted in space without shifting all the other objects in the simulation.

The process for which the simulations were prepared only required three files in a root directory: the Python script that creates everything; a template of the MCNP6 input file, modeling the XBI system and the phantom to be imaged, with the system starting at the center of the phantom; and a shell script template which submits the simulations to be run on the HPC. For every pixel in the image, the Python script will:

Create a new sub-directory

Copy MCNP6 template to each sub-directory

Edit the copied template in order to shift the XBI system inside the model so that its physical location is where the pixel is located for that sub-directory Copy the shell script template to the sub-directory and use it to submit the edited MCNP6 file to start running on the HPC.

Once all the simulations are finished, the Python script can then go into each sub-directory, pull out the results from the output file, and aggregate them into a single array with the same dimensions of the desired image. From there, the array can be analyzed, processed, or visualized like any other image.

For this study and all others discussed herein, MCNP6 was set to measure the fluence of photons crossing the face of each detector; detectors were not given any material properties. In this way, the data acquired by these simulations are not influenced by specific materials and their detection efficiencies. The results can be interpreted as if the detectors had perfect collection efficiency, thereby only the detector's dimensions can influence the photons collected. If specific detector materials were of interest, it's possible to post-process the data in order to account for detector efficiency effects.

Figure 2:
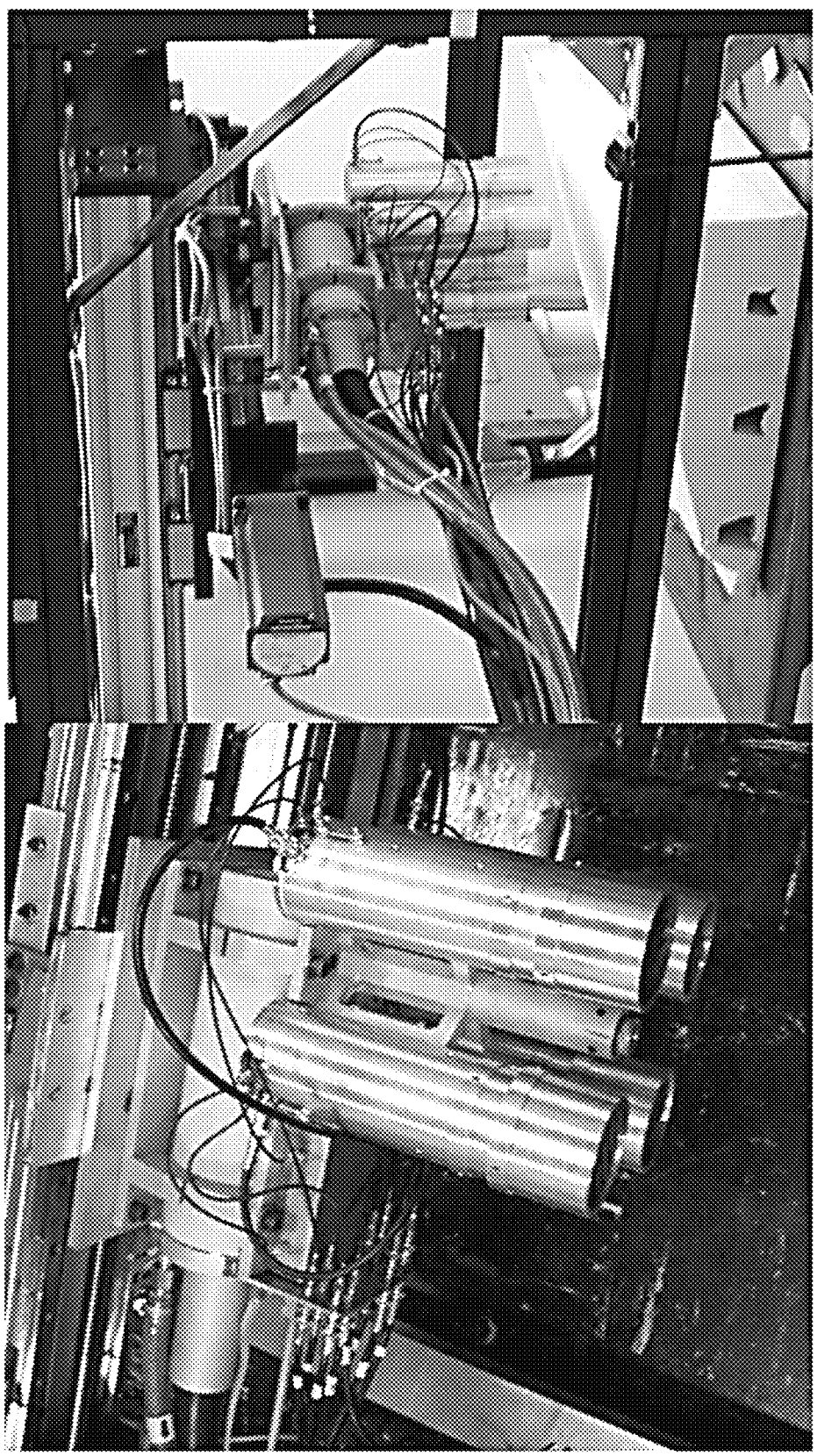
FIG. 2 shows an image of a XBI system prototype comprising a 1.5 mm diameter pencil-shaped beam using a 60 kVp X-ray tube spectra, with four NaI scintillator detectors arranged in a ring around the beam.

Two test cases were considered for the MCNP6 validation. The first case was based off the prototype XBI RSD system developed in the early 2000's at UF to create 2D images for the detection of voids and defects in industrial materials, such as the spray on foam insulation (SOFI) used on the NASA space shuttle. FIG. 2 shows an image of the XBI RSD prototype, which comprised a 1.5 mm diameter pencil-shaped beam using a 60 kVp X-ray tube spectra, with four NaI scintillator detectors forming a ring around the beam. Each detector had a 0.2 mm thick lead collimation sleeve placed around it. A 2.9 cm thick aluminum calibration plate with five 0.6 cm diameter holes drilled halfway into it served as the validation image.

The MCNP6 model sought to replicate the XBI RSD prototype system as closely as possible. One assumption made was the system was placed 1 cm away from the object surface. The length of the collimation sleeves were never mentioned either, so they were set so the detectors could see scattered X-rays at 0.7 cm and deeper inside the phantom. Also, a Matlab code called Spektr was used to try and mimic a 60 kVp X-ray spectra. However, without knowing the exact spectrum used by the prototype, it is uncertain how accurate the Spektr model was.

Figure 3:
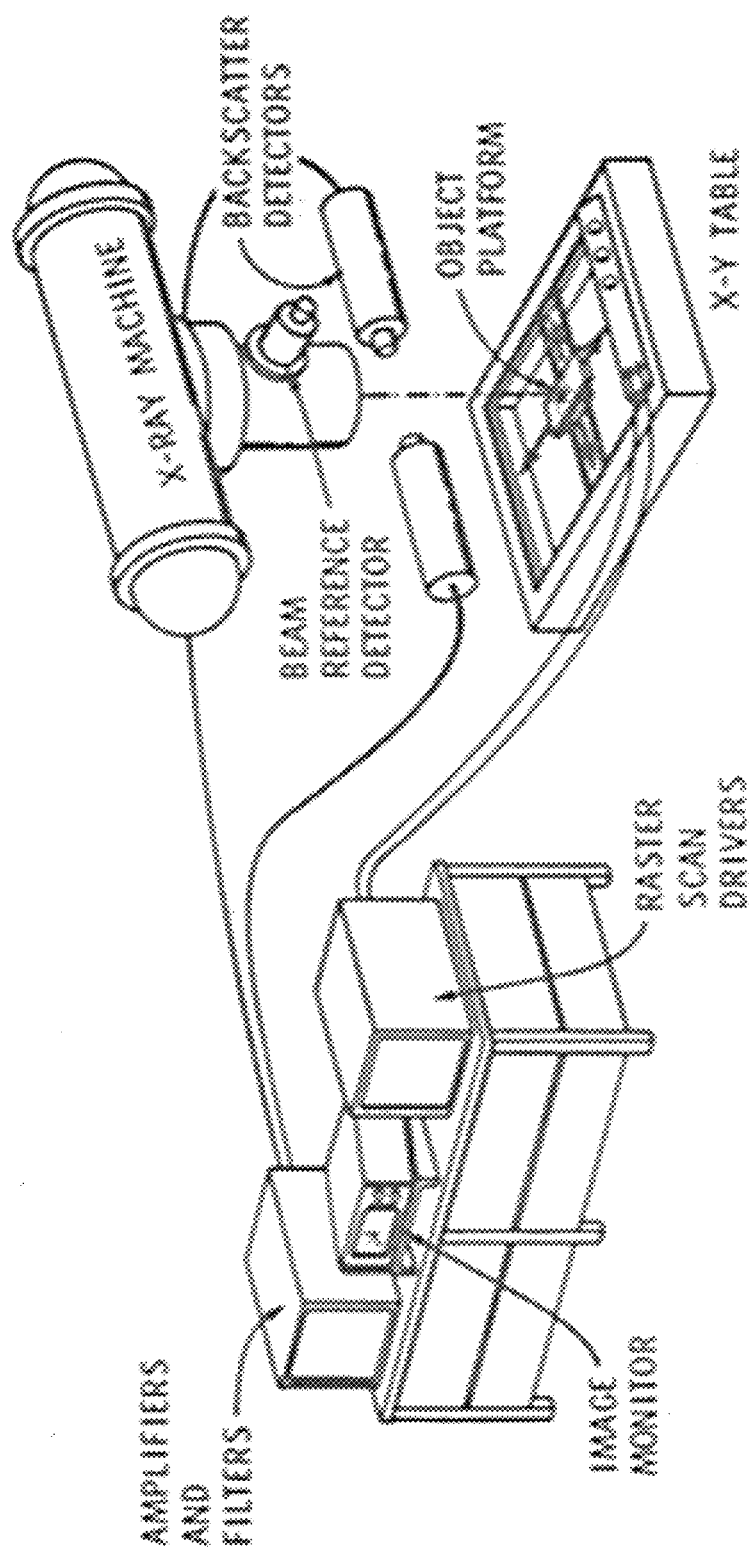
FIG. 3 is a schematic diagram of an XBI system described in a paper by B. C. Towe and A. M. Jacobs, entitled "X-Ray backscatter Imaging," published IEEE Trans. Biomed. Eng., vol. BME-28, no. 9, pp. 646-654, September 1981.
Figure 4:
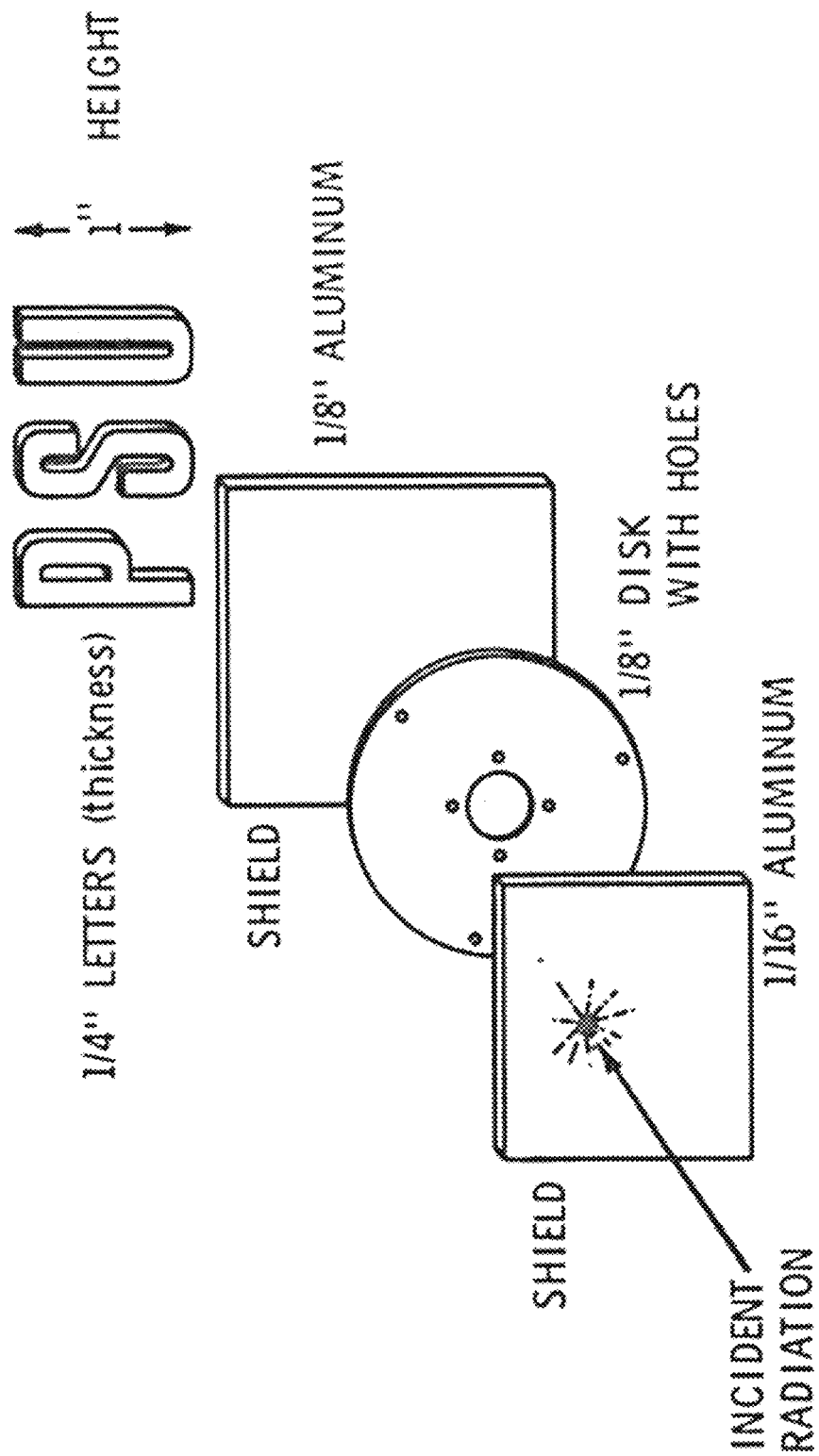
FIG. 4 shows a composite test object used in the XBI system shown in FIG. 3 to demonstrate 3-D imaging properties of the technique performed by the XBI system shown in FIG. 3.

The second test case was based off of an XBI design described by Towe and Jacobs. The concept of that XBI design was: to scan an image multiple times, at different X-ray tube voltages, in order to acquire images with different depth information, thereby achieving a form of single-sided tomography. A schematic of the system set up is shown in FIG. 3. The test image was based off of an experiment described in FIG. 4. The physical dimensions recorded in FIG. 4 were used to create a duplicate model in MCNP6. Other than the pencil-shaped beam being 1 mm in diameter, the rest of the system parameters were unknown. Therefore the same system model was used from the first test case, except all the collimation was removed and the pencil-shaped beam was adjusted to 1 mm. The technique involved multiple scans of the object at different X-ray tube voltages, so multiple spectra were created in Spektr for the different MCNP6 images. The paper mentioned using 40, 50, 70, and 100 kVp beam energies.

Figure 5:
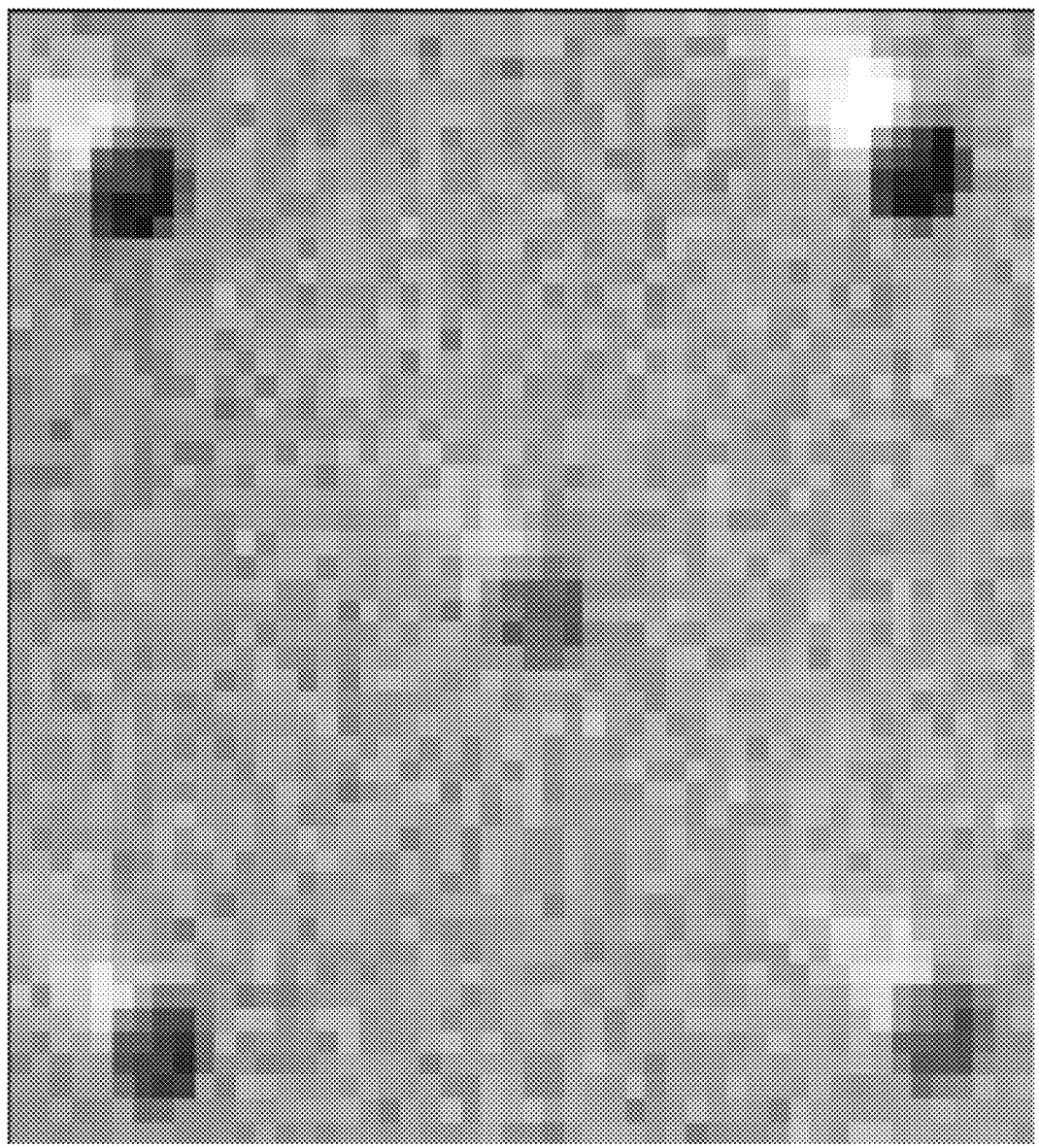
FIG. 5 shows an experimental image of the aluminum calibration plate used in the XBI system shown in FIG. 2.
Figure 6:
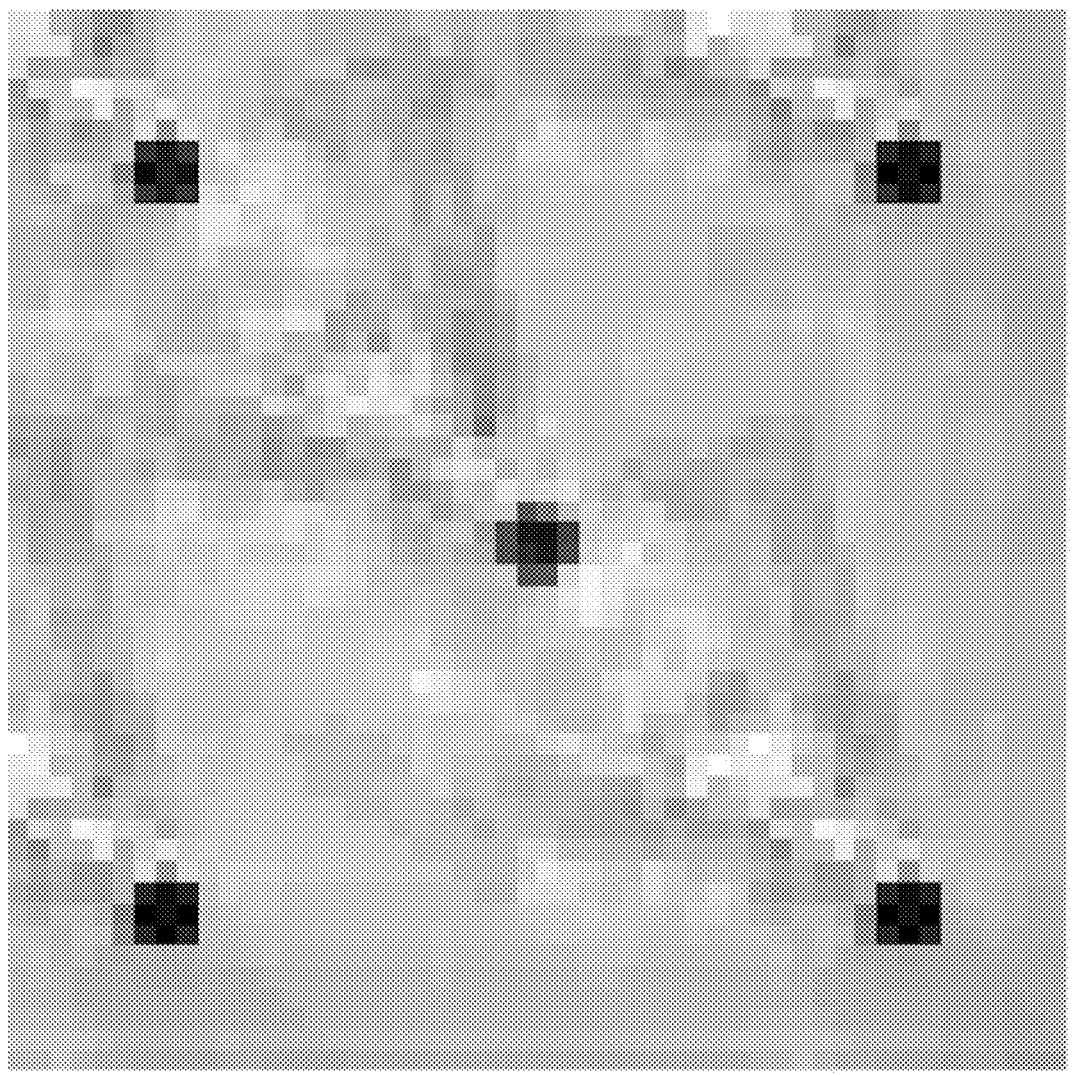
FIG. 6 shows an MCNP6 simulated image of the aluminum calibration plate used in the XBI system shown in FIG. 2.

The experimental image of the aluminum calibration plate for the first test is shown in FIG. 5, followed by the MCNP6 replication in FIG. 6. Data from only one of the four detectors was shown in the experimental test, so the corresponding detector from the MCNP6 model was chosen for comparison.

A visual comparison shows good agreement between the images of FIGS. 5 and 6, with the holes in the aluminum creating dark spots in the image. The holes create dark spots in the images because there is a lack of material there from which X-rays can scatter and contribute a signal for those pixels. Likewise, the same streaking artifacts are present in both images, although it is more severe in the simulated image. This is likely due to the system being much closer to the object surface in the model than what was actually done in the real scan. Streaks occur when there is information collected from only one direction during XBI. This is because of the two separate paths the photon must travel. When the primary beam is directly over the void, it is a dark spot due to lack of scattering. However when the system moves away—in this case towards the bottom-left—the void is now in the way of the secondary beam path since the detector is located towards the upper-right direction of the primary beam. This void provides a lack of attenuation for the secondary, scattered photons and thus allows for more photons to reach the detector, resulting in a brighter signal. The closer the system is to the object's surface, the longer the secondary path is inside the object, and so the longer the streaking artifact will be.

Figure 7A:
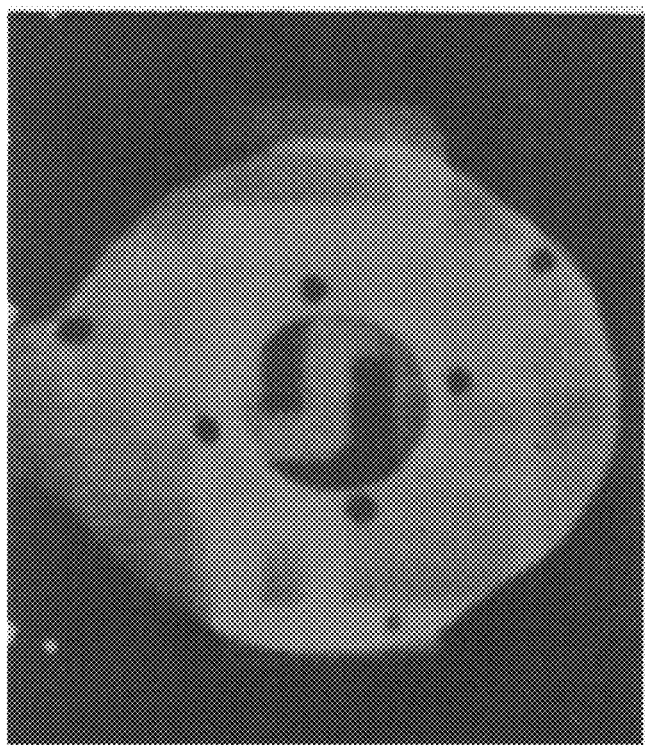
FIGS. 7A and 7B show two of the four images of the composite test object shown in FIG. 4, obtained by the XBI system shown in FIG. 3 at 40 kVp and the other at 100 kVp beam energy.
Figure 7B:
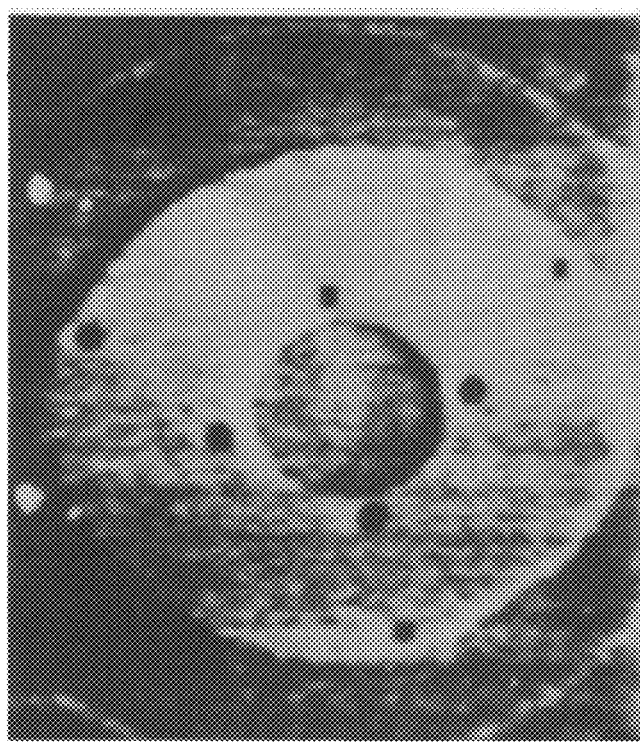
Figure 8B:
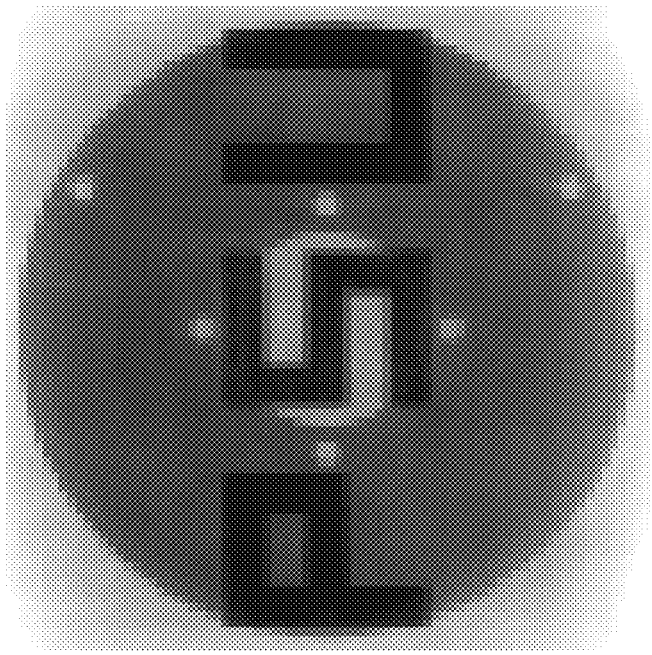
FIGS. 8A and 8B show the attempted MCNP6 replication of the composite test object used in the XBI system shown in FIG. 3.
Figure 8A:
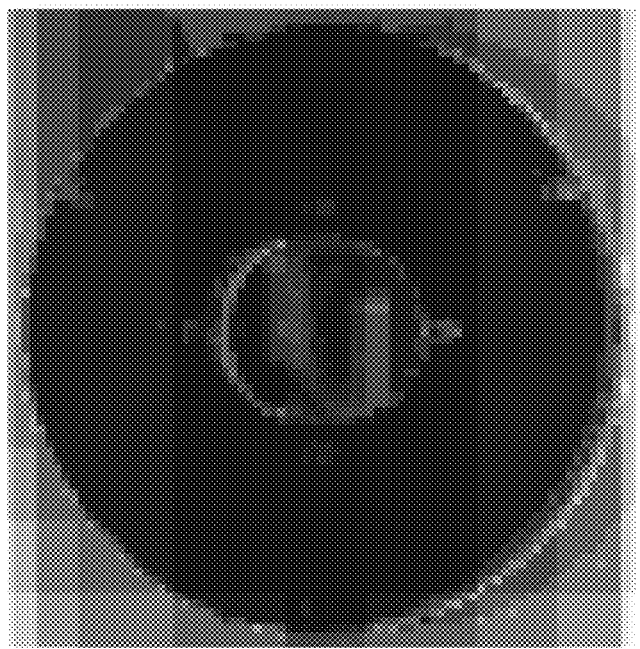

FIGS. 7A and 7B show two of the four images presented by Towe and Jacobs, one at 40 kVp and the other at 100 kVp beam energy. FIGS. 8A and 8B show the attempted MCNP6 replication. The biggest obstacle was that the simulated X-ray spectra provided significantly more image penetration than what was shown by Towe and Jacobs. Therefore, lower, mono-energetic X-ray images were taken in order to still prove that it is possible to perform depth sensitive imaging with X-ray backscatter inside MCNP6. Two possible explanations for the discrepancies in required X-ray spectra: the effect of unknown system geometry and detector efficiencies inside the experimental images required greater X-ray energies; and/or the energy spectra emitted from the experiment's X-ray tube is far different than what was attempted in the simulation model, using Spektr. Despite the one difference, it was clearly shown that modulating the X-ray energy enables depth sensitive imaging even in simulation.

Previous works have attempted to use Compton scattering as a means for performing 3-D imaging, but they rarely only used backwards scattering radiation and they achieved varying degrees of success. Typically, the systems utilized highly collimated detectors and photon sources, with and without the image processing, to extract depth information.

Although the majority of backscatter modalities have been designed to acquire 2D images, Towe and Jacobs showed that it is possible to obtain depth-sensitive information (the 3rd dimension in this case) by acquiring multiple images, each at a different X-ray tube voltage. When the average energy of the X-ray source (and therefore penetration depth) is changed, the signal, which is generated from a backscatter design, changes depending on the materials present in the object of interest. A form of image tomosynthesis can be achieved by taking multiple scans at different X-ray energies and observing the change in the image produced. However, the depth resolution of such an image is neither precise nor uniform, since it relies on the statistical nature of photon interactions. It also requires multiple exposures/scans, which increases both imaging time and dose.

At least two primary objectives are achieved by the experiment and simulation described herein. The first objective is to perform a parametric study on X-ray energy and its associated backscatter signal depth for materials relevant to medical imaging and non-destructive testing. This provides a better understanding of the capabilities of this backscatter tomosynthesis technique. The second objective is to perform a proof of concept for an improvement upon this technique, which inverts the known process described above. In particular, instead of performing multiple scans at different tube voltages, the technique described herein requires just one scan at a set voltage. The detectors use energy discrimination in order to measure the signal generated from different depths within the object. This improvement reduces both scan time and radiation dose.

This simulation was conducted using the radiation transport code MCNP6. The modeled XBI system was a simple pencil-shaped beam X-ray source surrounded by four cylindrical detectors, each 5 cm in diameter. The center of each cylindrical detector was located 7 cm away from the center of the pencil-shaped beam and 1.88 cm away from the surface of the phantom being imaged. Detector faces were parallel to phantom surface. The same methods discussed above were used to form simulated images.

This simulated XBI system having this configuration has relatively slow image acquisition, but it also has a relatively uncomplicated design, allowing for fine-tuning of image resolution with the fewest factors to complicate a backscatter signal. For a pencil-shaped beam system, the image resolution across the scanning dimensions (X and Y in this study) is determined by the beam diameter (1 cm for the parametric study) and less so by the detector size. Since the system scans in 1 cm steps, the depth discrimination resolution was at best 1 cm for this study. By simply using a smaller beam, one can increase image resolution at the cost of increased scan time. The photon source of the MCNP6 simulations was biased so that it modeled a parallel beam, generating photons only in the negative Z direction towards the test phantoms, thus removing the signal degradation caused by an isotropic source term.

An image was formed by tracking the combined surface current tallies of the four detectors for each scan point (pixel); therefore, each pixel had the units of photons crossing the surface per starting source photon. Thus, for a known source intensity, the pixel data provided an estimate for the number of photons entering the detectors. By measuring the photon current over the surface of a detector face, information is acquired independently from detector material, volumes, and efficiencies. However, common scintillation detectors (e.g., sodium iodide) have been effectively used in past experimental systems.

Figure 9B:
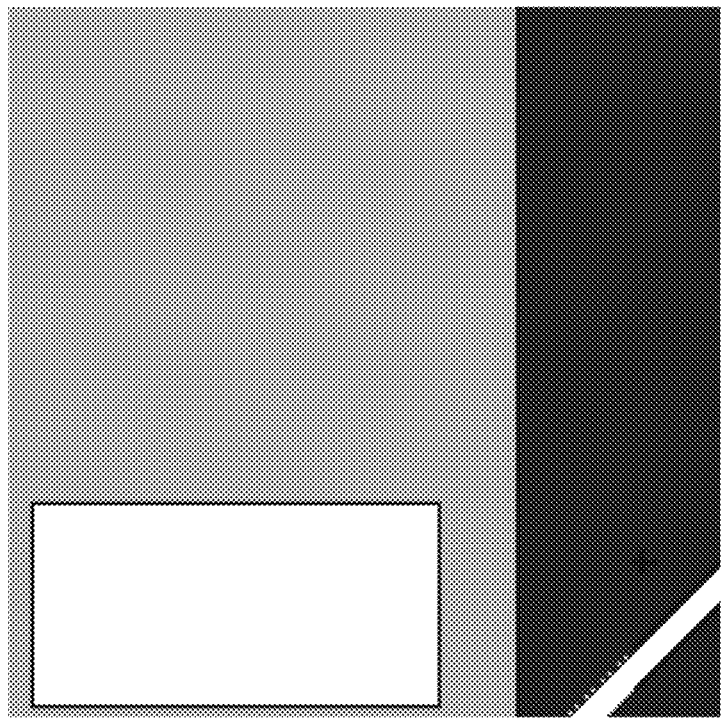
FIG. 9B shows a parametric study phantom in the YZ plane.
Figure 9A:
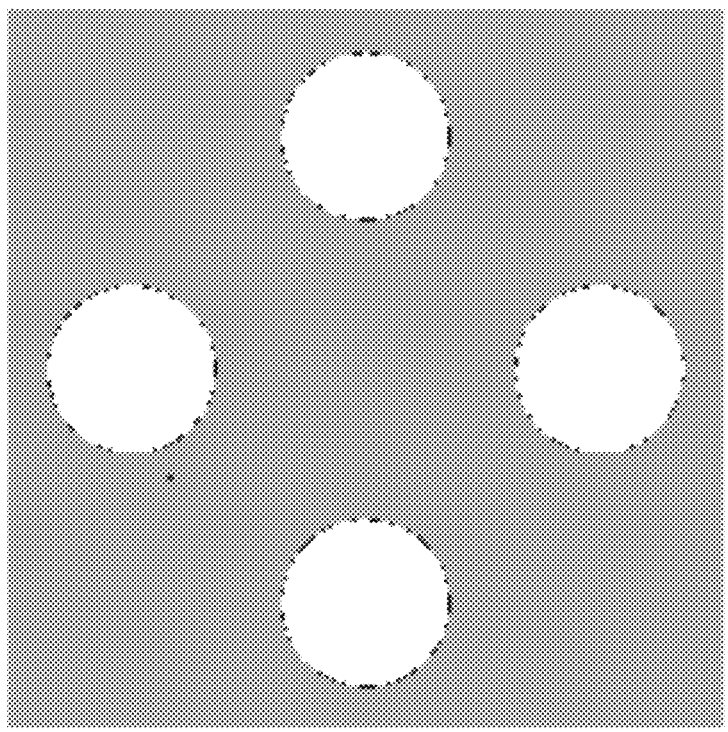
FIG. 9A shows a cross-sectional view in the XY plane of a simulation of four X-Ray detectors in MCNP6 in an XBI system, where a pencil-shaped beam source would be at the center of the ring of detectors.

The four detectors were arranged in a "cross-hair" geometry, and their signals were summed in order to remove the shadowing effects that occur in backscatter imaging when images are collected from only one scatter direction. When images are collected from orthogonal positions around the beam, the cumulative signal removes the shadows apparent from just one detectors image. FIG. 9A shows a cross-sectional view of the four detectors, where the pencil-shaped beam source (not shown) would be at the center of the ring of detectors.

Since a pencil-shaped beam system raster scans over its object to form 2D images, a separate MCNP6 simulation is used for each position of the system. In these simulations, the system scanning plane was the XY dimension (depth is Z dimension). For the purposes of speed, a 14 cm by 5 cm scan was used (70 pixels per image). One image was formed for each of three test phantoms for X-ray energies ranging from 10 keV to 200 keV (in steps of 5 keV). Mono-energetic X-ray sources were used in order to accurately define depth penetration.

For the subsequent proof of concept, the pencil-shaped beam was reduced to 5 mm in size while detector dimensions were kept retained. The X-ray spectra were modeled after a 150 kVp unfiltered lead target X-ray tube, using the computational tool Spektr. The system raster scanned a 28 cm by 18 cm (56 by 36 pixels) region over the test phantom.

Three test phantoms were used for the parametric study: (1) a block of soft tissue with a cylinder of air; (2) a block of soft tissue with a cylinder of compact bone; and (3) a block of aluminum with a cylinder of air. FIG. 9B shows a cross-sectional view of one of the phantoms. In each case, the cylinder feature (having 0.35355 cm radius) is embedded inside the surrounding material at a 45° angle so that the top of the cylinder is at the surface and the bottom is located 10 cm deep inside the block. In this way, each scan step (pixel) of 1 cm in the X direction corresponds to the feature being located 1 cm deeper in the block, allowing for a controlled measurement of depth sensitivity for a given X-ray energy. The phantom blocks were made large enough to ensure uniform scattering at the imaging volume boundaries. The X-Z plane shown in FIG. 9B corresponds to the signals collected in the middle row (row 2) of the acquired images. The four other rows correspond to when the system is scanning over the bulk, homogeneous section of the phantoms (i.e., no feature is present underneath the systems pencil-beam).

The materials used in these phantoms cover a range of imaging situations. Soft tissue, air, and bone are what primarily make up the components found in diagnostic images of bone, lungs, or gastrointestinal tract. Aluminum is a common material used in products and serves a good first example of the non-destructive testing of metallic objects, scanning for voids and defects.

Figure 10A:
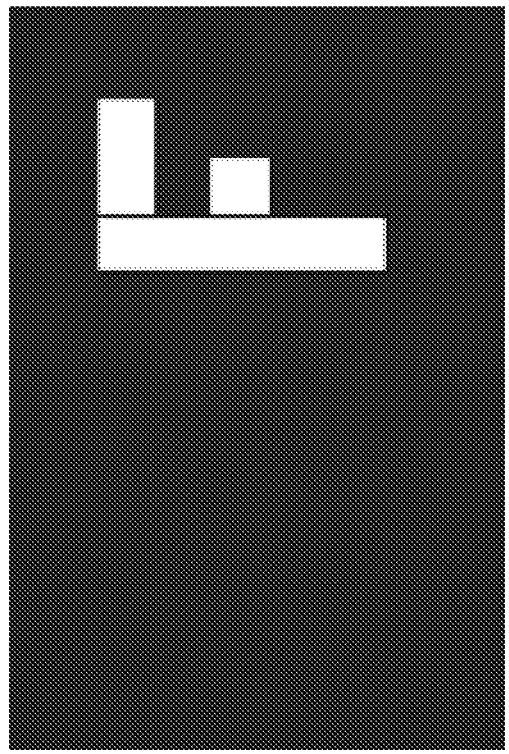
FIGS. 10A and 10B show cross-sectional views in the X-Y dimension of the phantom in MCNP6 at 6.5 cm deep and 8.5 cm deep, respectively.
Figure 10B:
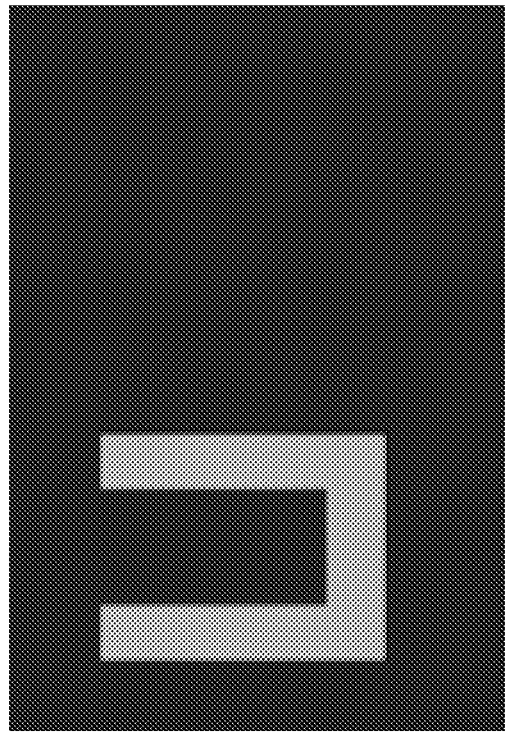

A tissue test phantom was used to test the tomosynthesis proof of concept. The letters U and F were embedded 6 cm and 8 cm deep in the tissue, respectively. Each letter was 2 cm thick and spanned a depth of 1 cm inside the phantom. The letter U was made of air, whereas the letter F was made of compact bone. These depths were chosen based on the results of the parametric study and were another way to verify the depth penetration of the X-ray source. FIGS. 10A and 10B show cross-sectional views in the X-Y dimension of the phantom in MCNP6 at 6.5 cm deep and 8.5 cm deep, respectively.

For the parametric study, a relatively simple version of the binning algorithm discussed above with reference to FIG. 1 was developed to analyze the acquired images and determine how deep the feature in a given phantom is distinguishable from the surrounding bulk material. The algorithm defines "distinguishable" as any pixel intensity that is greater or less than three standard deviations away from the mean pixel intensity. Mean pixel intensity and standard deviation are calculated from all the pixels located in the first and last two rows of the image (i.e., rows 0, 1, 3, and 4). These rows represent the background for the image (i.e., signal from bulk homogenous material of a phantom).

Figure 11:
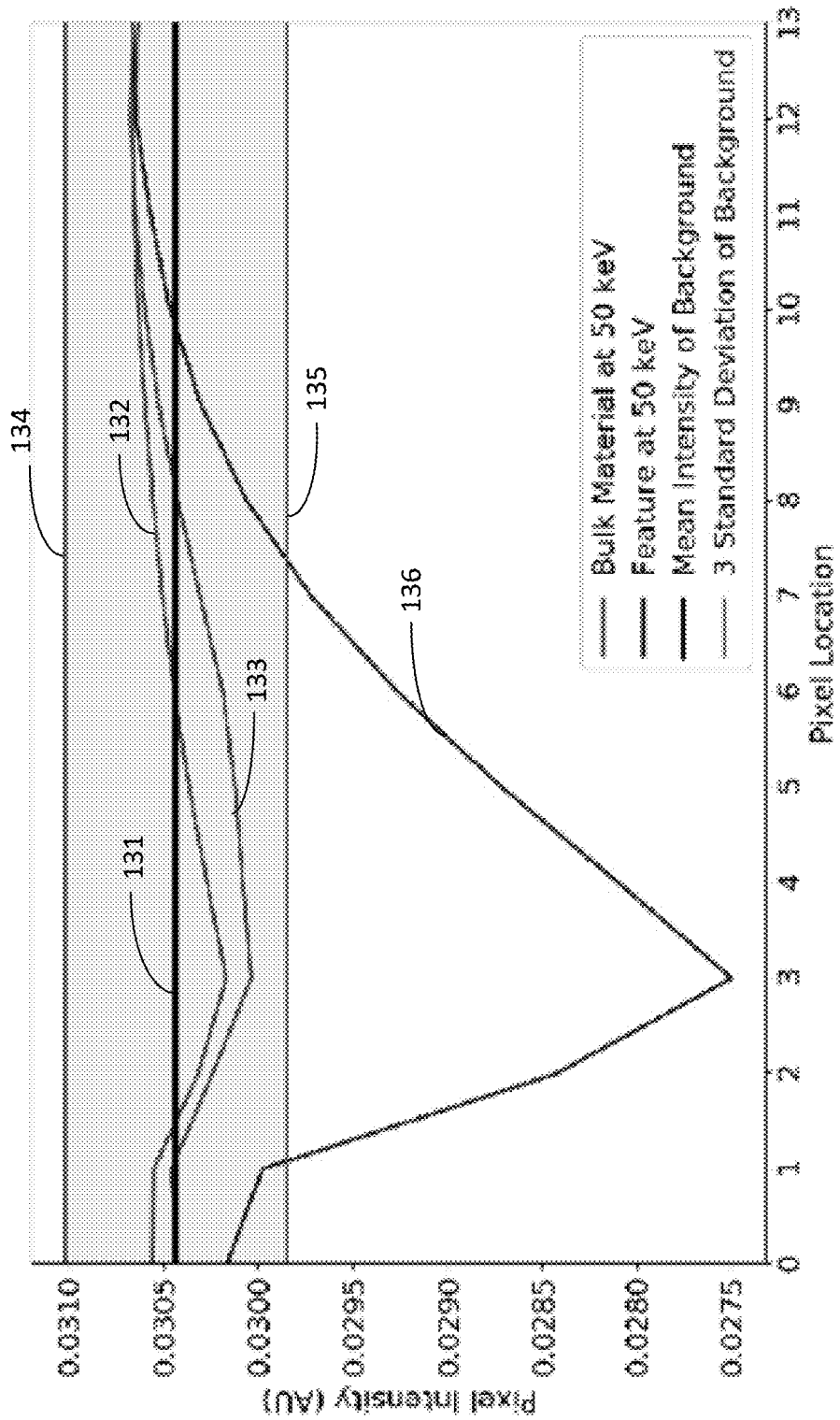
FIG. 11 is a graph that illustrates depth distinguishability achieved by the XBI system in accordance with an embodiment by using an energy binning algorithm.

Because the feature inside the imaged phantom is located in the middle row (row 2), only the pixels in row 2 are checked to determine which intensities are greater than three standard deviations away from the mean. The location of the pixel farthest along this row (subtract 2 pixels) is the depth in centimeters in which the feature is still distinguishable from its surrounding material. The pixel index starts at 0, and the first three pixels in the row either do not contain the feature or it is at the surface of the phantom, which is a depth of 0 cm, and should not be counted; thus, 2 pixels are subtracted. FIG. 11 is a graph of pixel location vs. pixel intensity that illustrates this theory using the image obtained from the tissue/bone phantom with 50 keV photons. Plot 131 is a plot of the mean intensity of the background. Plots 132 and 133 are plots of the of pixel location vs. pixel intensity for the bulk material at 50 keV. The region between lines 134 and 135 corresponds to the standard deviation of the background intensity. Plot 136 is a plot of the pixel location vs. pixel intensity for the feature at 50 keV. Pixel location 7 is the farthest pixel outside the statistical fluctuations of the soft tissue background. Therefore, 50 keV photons can distinguish bone from soft tissue up to a depth of about 5 cm.

Figure 12A:
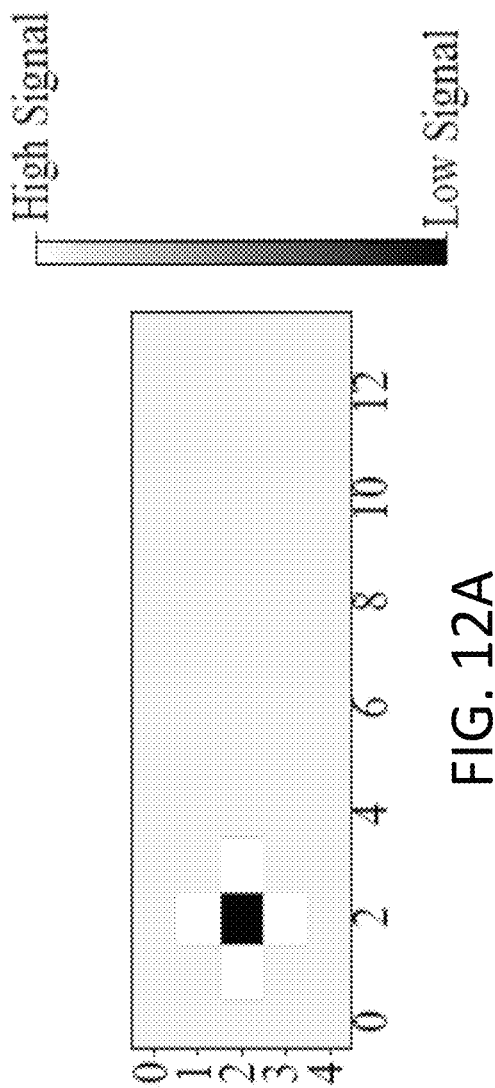
FIGS. 12A and 12B show raw images of a soft tissue phantom with a cylinder of air acquired at 10 keV and 70 keV X-rays, respectively, by an XBI system in accordance with an embodiment and processed with an energy binning algorithm in accordance with an embodiment.
Figure 12B:
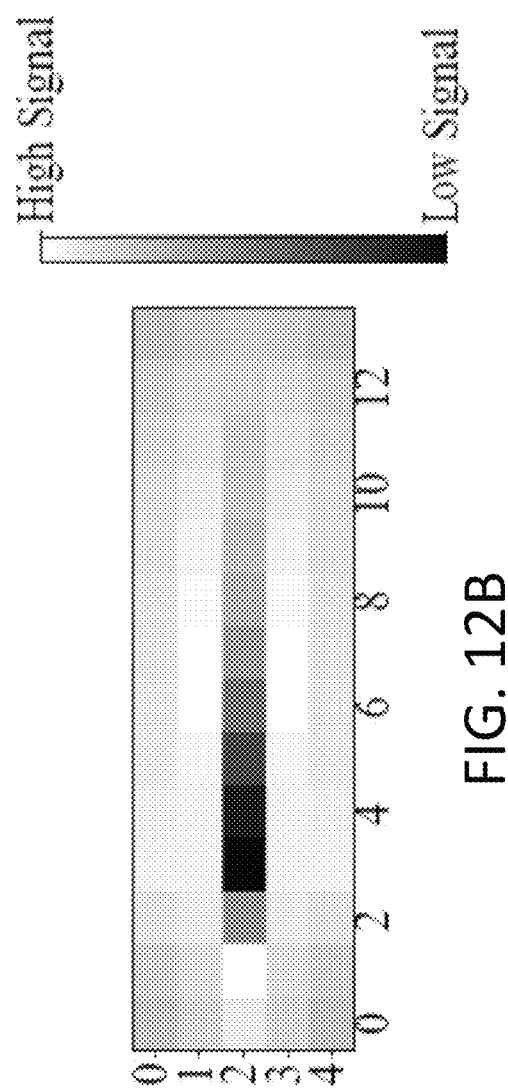

FIGS. 12A and 12B show the raw images of the soft tissue phantom with a cylinder of air at 10 keV and 70 keV X-rays, respectively. The system scan began 2 cm (2 pixels) behind the cylinder of air. The interrogation source energy affected what was visible inside the object being imaged. As FIG. 12B shows, the 70-keV image is noisier with no clear depth cutoff; this is partly due to the system resolution and limited number of pixels in the image. However, by using the binning algorithm described previously, the signal from the air feature dropped off to background levels at approximately 6 cm. The air inside the phantom caused a lower signal than the bulk material because of its low density; thus, photons were less likely to interact with it. This behavior was also observed inside the aluminum/air phantom.

Figure 13:
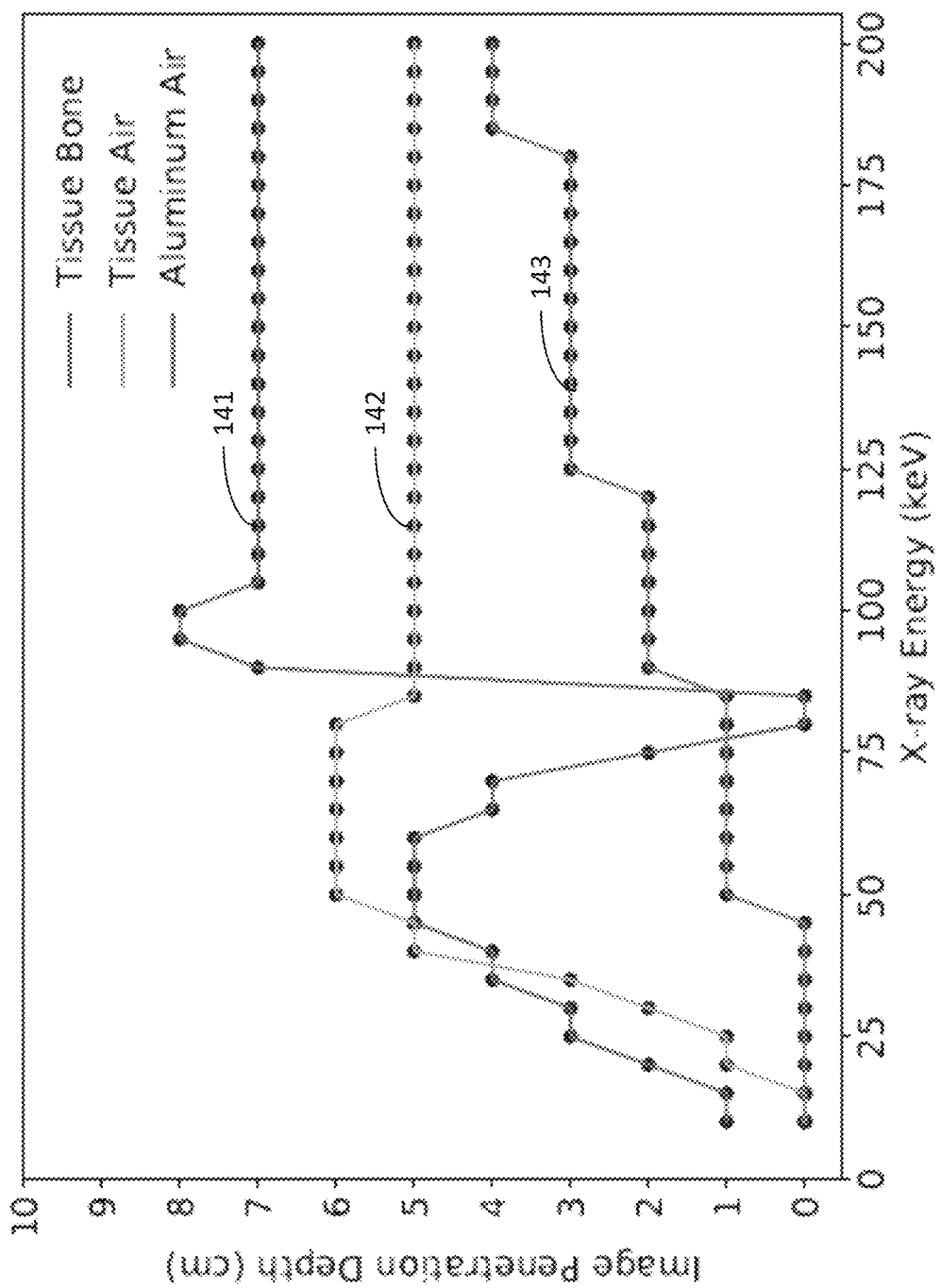
FIG. 13 is a plot of image penetration depth versus X-Ray interrogation energy for images acquired by an XBI system in accordance with an embodiment.

FIG. 13 is a graph of X-ray energy vs. image penetration depth that shows the association between signal depth and X-ray energy for each phantom. Plot 141 corresponds to the tissue/bone phantom. Plot 142 corresponds to the tissue/air phantom. Plot 143 corresponds to the aluminum/air phantom. The low-energy photons (40-90 keV) penetrated deeper into the soft tissue when air rather than compact bone was present. Notably, because bone is denser than the material surrounding it, the penetration depth for the soft tissue phantom with bone dropped to zero at 80-85 keV and then spiked again. For low-energy ranges, the photoelectric effect absorbs X-rays more frequently than it scatters them, thereby reducing bone signal. However, beyond 50 keV, Compton scatter becomes the dominant interaction and bone will begin emitting more signal than the surrounding soft tissue. During this transition period, bone eventually generates a signal intensity comparable to soft tissue, causing it to be indistinguishable from its surroundings.

Figure 14:
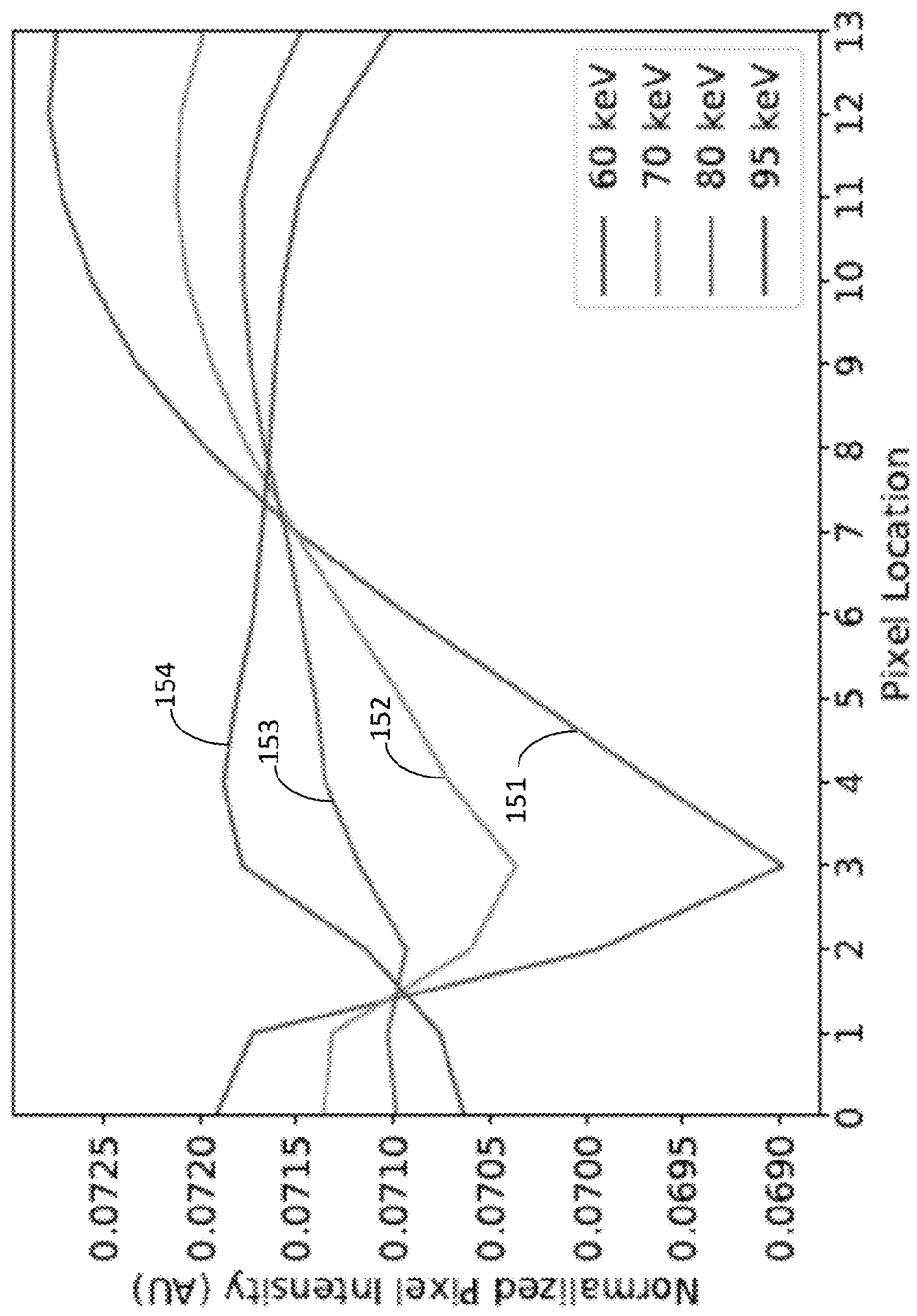
FIG. 14 is a plot of normalized pixel intensity versus pixel location along a middle row of images acquired from a tissue/bone phantom by an XBI system in accordance with an embodiment.

FIG. 14 captures this phenomena of transitioning signal intensity. Plots 151, 152, 153 and 154 correspond to pixel location vs. normalized pixel intensity for voltages of 60, 70, 80 and 90 keV, respectively. The 80 keV pixels clearly have much smaller changes in intensity as compared to other energies. This shifting of a features signal from low to high intensities relative to its surroundings, with increasing X-ray interrogation energy, is not exclusive to bone embedded in soft tissue. This phenomena should be inherent in any backscatter imaging scenario where high electron density materials are surrounded by a lower electron density medium. These results show that there is a limited depth at which bone and air can be distinguished from soft tissue and increasing photon energies yield no more information: 5 cm and 7 cm for air and bone, respectively. Deeper depth information was achieved for specific ranges of photon energies: 6 cm at 50-80 keV for air and 8 cm at 95-100 keV for bone.

With reference again to FIG. 13, an interesting result shown is the seeming plateau of depth distinguishability for tissue/air (plot 142) and tissue/bone (plot 141). The hypothesized explanation for this occurrence is a combined effect from the photon's mean free path in the tissue and the detector's placement. The depth at which the higher energy photons interact inside tissue, combined with the detector's distance from the incident beam, causes signals to only be collected when photons scatter at angles greater than about 140°. These kinds of scatter angles are increasingly unlikely at these higher photon energies, where forward scattering dominates. By this logic, the plateau has not yet occurred in the aluminum phantom (plot 143) because even at high photon energies, the mean free path is still shallow enough that scattering angles aren't so severe.

Image penetration was more consistent, with a gradual incline for the air-filled aluminum phantom (plot 143); overall it was lower than the other phantoms at the photon energies considered due to aluminum's much higher electron density. Significantly higher X-ray energies are necessary for depth-sensitive information in industrial applications containing aluminum and other high electron density materials, depending on the desired depth.

Because the Spektr tool can only model an X-ray spectrum up to 150 kVp, a tissue test phantom was used; it has lower attenuation coefficients than aluminum at those energies. The average energy for the spectrum was 57.6 keV. At that energy, photons have a mean free path of 4.83 cm in soft tissue (based on mass attenuation data from NIST). Air and bone letters were imbedded in the tissue with their max depths being based on the results in FIG. 13 (6 and 8 cm, respectively). At approximately 90 keV there was a clear cutoff between air and bone image depth penetration. Therefore, two energy bin groups were used for the detector: (1) any signal less than 90 keV and (2) any signal above 90 keV.

Figure 15A:
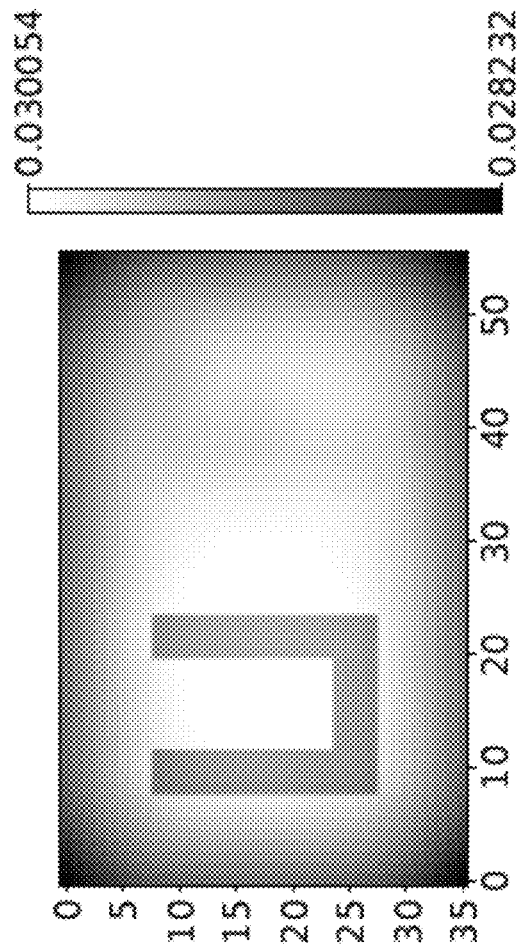
FIGS. 15A and 15B show resulting images after a phantom was scanned by an XBI system in accordance with an embodiment and the signals were binned into their respective energy groups by an energy binning algorithm in accordance with an embodiment.
Figure 15B:
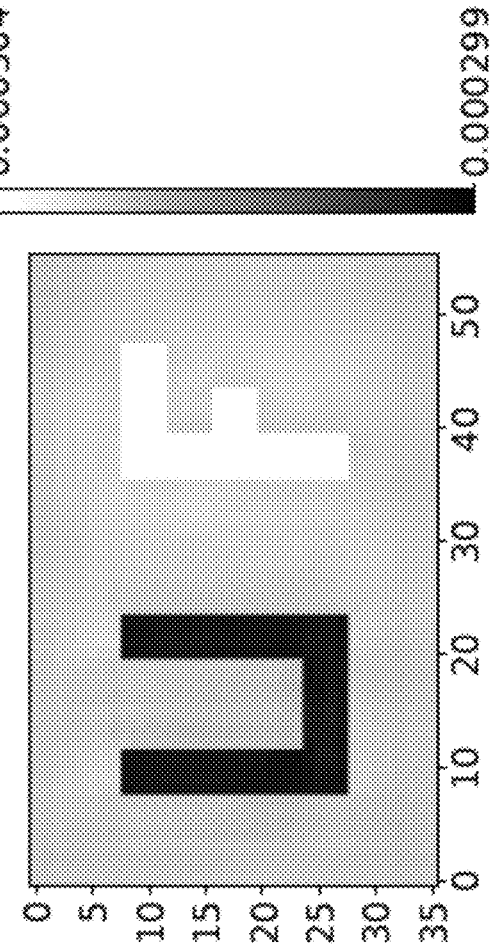

FIGS. 15A and 15B show the resulting image after the tissue/air/bone test phantom was scanned and signals were binned into their respective energy groups. The values shown on the horizontal and vertical axes of these images represent the index number of the scan point; multiplying this index number by the width of the scan step (pencil beam width) would provide the physical dimensions of the scanned area. When the system measured photons less than 90 keV, only the letter U was present (FIG. 15A), which means the system only sees up to 6-7 cm deep. But when it measured photons greater than 90 keV, the letter F was also visible (FIG. 15B), so the system can now see up to 8-9 cm deep. This is another example of the result of the processing logic 110 of the XBI system 100 shown in FIG. 1 performing the aforementioned binning algorithm to obtain depth-sensitive information. The letter U produces a low signal because of the low density of air. The letter F, which is composed of compact bone, provides a brighter signal, as was observed in the parametric study at those energy ranges.

The average backscatter signal in the lower energy and higher energy groups was about 2.95% and about 0.0245% of the primary beams particle flux, respectively. This corresponded to an energy fluence of about 1.45 keV per starting source particle for the lower energy group and about 0.02311 keV per starting source particle for the higher energy group. The total energy fluence coming from the incident beam was about 57.6 keV per starting source particle. By dividing the energy fluence at the detector face by the energy fluence projected at the phantom, one obtains a collection efficiency of about 2.55%.

It can also be seen that the range of signals in the high energy group is quite small, only about a 1.5% change from the lowest signal to the highest signal in the image. If this were to be the case for a real system acquiring this image, then a photon source with an intensity of $10^9$ photons per scan point would be necessary in order to acquire enough counts so that the image contrast between the lowest and highest signal are greater than their associated uncertainties.

Figure 16:
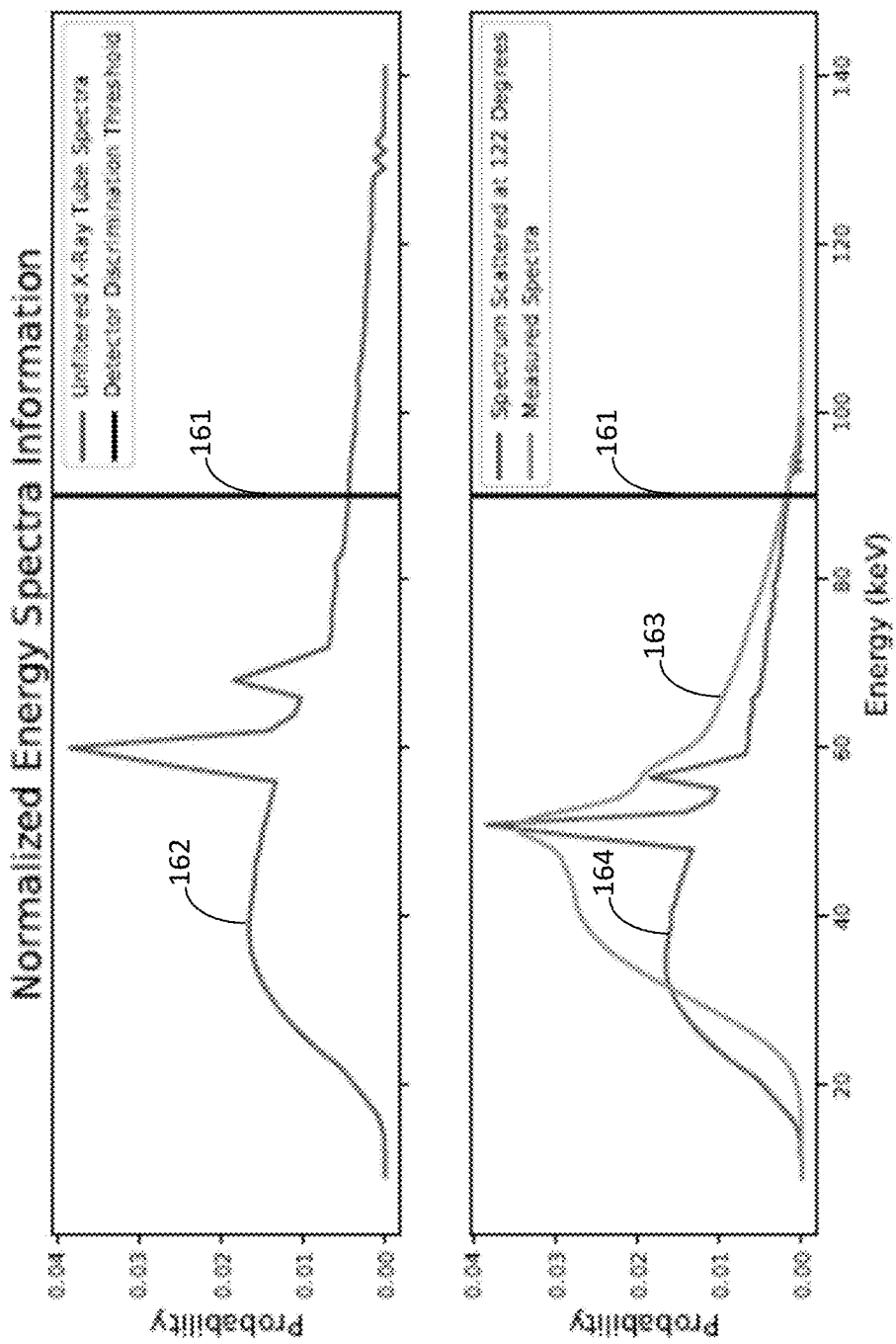
FIG. 16 shows probability distributions of an initial source spectra used to investigate a test phantom, a measured spectra at the detector faces and the initial spectra scattered by 122 degrees.

This drastic reduction in signal for the higher energy group can be explained by FIG. 16. Plot 162 shows the energy spectra of the X-rays leaving the X-ray source and heading towards the object to be imaged, modeled inside MCNP6. The bottom distribution (plot 163) represents the normalized energy spectra that was collected at the detector face during the image acquisition. The MCNP6 calculated spectra in plot 163 appears to correspond well to an X-ray energy distribution like that seen in plot 162 if it were scattered by the atoms in the object by an angle of 122°, shown by plot 164. As can be seen by the black vertical lines 161, applying a 90 keV threshold value means only 11% of the initial spectra 162 (and 1% in the scattered spectra 163) is placed in the high energy group. It was found that shifting the threshold down to 60 keV maintained image quality and depth discrimination while increasing the signal collected in the high energy group by an order of magnitude. As stated above, it was found that the measured energy spectra 163 aligns well with the distribution 164 one would get if the initial 150 kVp spectra (162) was scattered by 122°, and then had its low energy components filtered. This filtering is what would be expected to happen as these scattered photons have to leave the phantom, passing through more material on its way to the detector faces.

Based on the above experimental and simulation results, it can be concluded that X-ray backscatter imaging only needs single-sided access to an object and has the ability to acquire images beyond its normal 2-D capabilities with just one scan of an X-ray source and spectral detector. This tomosynthesis technique is a marked improvement over its predecessor, which required multiple scans at different tube voltages. By performing a parametric study of photon energies on the depth sensitivity of images acquired for specific materials, a database can be developed to aid in the design and use of backscatter imaging for 3-D interrogation for a wide range of materials and applications.

The materials used in this study were chosen for their relevance to applications in medical imaging and non-destructive testing, although the inventive principles and concepts are not limited to use in these applications or any other particular applications. Significant penetration was acquired (up to 5-6 cm) with moderate X-ray energies (40-55 keV) in organic materials, such as compact bone, soft tissue, and air; however, bone was most visible at energies greater than 90 keV. These energy ranges are easily achievable with standard X-ray sources. However, there appears to be a limited depth at which air and bone can be distinguished from the surrounding soft tissue. For industrial materials, such as aluminum, much higher X-ray energies are needed for significant depth information. Although this study used a collimated pencil-beam of radiation, other source/detector geometries may be used in order to reduce scanning times.

To further improve this study, photon energies beyond 200 keV for aluminum phantoms were evaluated. At higher energies, the photoelectric absorption becomes negligible but the probability for backwards scattering photons also decreases. It would be beneficial to investigate the absorbed dose received to organic materials for images acquired in this study and compare that with standard imaging techniques, such as radiographs and CT scans. The parametric study performed here can be expanded to many more materials, such as wood, concrete, and other organs. Also, entirely new parametric studies can be performed that investigate how depth penetration and depth resolution are affected by detector size, placement, and materials.

The choice of the X-Ray source and X-Ray detector geometries for the XBI system has a set of tradeoffs between acquisition time, resolution, and signal to noise ratio (SNR). As discussed above, pencil-shaped beam geometries have good resolution, but slow acquisition time. Fan-shaped beam geometries are discussed below, specifically plane-by-plane imaging, which provides faster imaging, but at the cost of lower resolution and lower SNR.

The XBI system to be discussed now is that of an X-Ray source that emits a fan-shaped beam and a 2-D X-Ray detector array having a collimation grid secured to a front face thereof. In this case, the term 2-D refers to the two-dimensional detector array, which enables the acquisition of a 2-D signal for every step the system takes: one dimension across the object's surface; one dimension into/inside the object; the third dimension being the mechanical scanning of the system across the object. A single scan point is 2-D (albeit one dimension is depth), but when combined with multiple scan points, a 3-D image is generated. This system is likely to be more useful than a pencil-shaped beam source in applications where relatively large areas must be scanned in a reasonable amount of time. However, formulating a collimation grid that is optimized for depth sensitive imaging is time consuming and prone to error if it has to be done manually for every design iteration. Therefore, this is an ideal situation for the development and use of a code package that will do the heavy lifting and allow the user to focus on the system's design parameters, such as resolution and detector dimensions.

The following discussion serves as an overview of the Python toolkit called backscatter2D, which was developed for the design of 2-D XBI systems, conversion into MCNP6 inputs, and subsequent image formation and analysis of the simulation outputs. A simple test is performed before moving on to the investigation of different scanning methods for 3-D imaging, discussed in further detail below.

Code Description

The toolkit/application package was written in Python and is called backscatter2D. Within the backscatter2D toolkit/application package, there are currently seven modules: a system design module; an MCNP module; a visualize module; a matplotting module; a tally reader module; an hpc utils module; and a reconstruct module. The focus of the following code description is about the system design module, with brief mentions of the other modules when necessary. The reconstruct module is also discussed below, when it is specifically used.

The system design module utilizes object-oriented programming, creating a class for each of the components in the 2-D XBI system, namely a fan-beam source, a detector array, and a collimation grid. The collimation grid can either be an optimized grid or a uniform grid. A uniform grid is one where the collimators are all the same length, for every row in the 2D detector array. An optimized grid represents collimators whose length are adjusted at every row in the 2-D detector array such that the pixels in each row are better focused on a specific depth in the object. There is also a class for the system as a whole called BackscatterSystem, which is just a composition of the previously mentioned classes except for added attributes, such as step size. The step size attribute determines the distance of each step the system takes when it is scanning over an object, which describes the resolution in the X dimension of the images acquired. In this toolset, the X dimension refers to the scanning dimension, Y dimension is the breadth of the fan-beam and detector width, and Z dimension is the height/depth. Step size also plays a role during MCNP input formulation because a collimator for the photon source is used to shape it into a fan-beam. Since the source is divergent, the fan-shaped beam broadens in the X dimension as is penetrates deeper into the object. Therefore, collimators are designed so that the fan-shaped beam is as broad as the system step size when it has penetrated a maximum depth inside of the object. This maximum depth is an attribute of the collimator class, discussed later. Tables 1 and 2 below give brief descriptions of the attributes used for each class in the design of a 2-D XBI system.

When all the components of the XBI system have been designed and placed inside of a BackscatterSystem instance, BackscatterSystem can perform some simple parameter calculations and store them in a dictionary called depths. Such parameters include: depth range a pixel can see for each row in 2D array; estimated resolution of pixels in the Y dimensions, for each row; and depth location that each pixel center is looking at inside of the object under investigation.

The photon source is handled in the toolkit by a class called XRayFanBeam. Its attributes are listed below in Table 1. X-ray is used in the naming convention because it is assumed that X-ray sources will be the most common type of radiation source used in backscatter imaging. However, it is entirely acceptable to use a mono-energetic source that is more akin to imaging with gamma emitting radioisotopes, which have been used before in Compton scatter imaging and densitometry. It can either be passed a single energy (in MeV) or it can be given a path to a file name containing an energy distribution. The distribution is written in the file as one entry per line and each entry contains two space delimited values. The first value is the energy of the photon (again in MeV) and the second value is the frequency in whatever units desired. Once the file is read and converted into a 2D array, it will create another array that normalizes the distribution based on the frequencies provided. This array will be used to create a source definition in MCNP with a varying energy distribution.

TABLE 1

List of variables required from user for XRayFanBeam class.

| Variable | Description (Units) |
|---|---|
| energy | Either a mono-energetic source (MeV) or an energy distribution (array[MeV, Frequency]) |
| $O_F$ | Offset distance of the photon source from the object surface (cm) |
| $\Phi_F$ | Half angle describing the breadth of the fan-beam (degrees) |

TABLE 2

List of variables required from user for Detector class.

| Variable | Description (Units) |
|---|---|
| $N_H$ | Number of pixels (rows) in the height of the detector array |
| $N_W$ | Number of pixels (columns) in the width of the detector array |
| $P_H$ | Height of a single pixel in the detector array (cm) |
| $P_W$ | Width of a single pixel in the detector array (cm) |
| $\theta_D$ | Angle of detector array from the surface of the object (degrees) |

The surface offset distance and half angle attributes determine the shape of the fan-beam. A larger half angle means a wider fan and a half angle of 0° creates a pencil-shaped beam. The offset distance merely describes the location/height of the photon source, which is needed when creating a source definition in MCNP. It should be noted that if the fan half angle and surface offset are not correct, it is possible the breadth of the fan-shaped beam at the object's surface will not be as long as the breadth of the desired detector width, meaning not all the pixels can be correctly imaged inside the object. This can be mitigated by first designing the detector in the toolset and then passing it to an instance of the XRayFanBeam class while calling its function that can optimize either its surface offset or half angle based on the detector's dimensions.

The matplotting module provides an X-Ray spectrum method that lets the user view their imported energy distribution to see what it looks like.

The Detector class contains the data regarding the dimensions and geometry of the 2-D detector array. It is a simple class and is the basis for the design of the collimators in the collimation grid. Table 2 above summarizes the class' required attributes. Besides containing information on the size and number of pixels in its array, it contains an important attribute called the detector angle. An angle of 0° means the detector face is parallel to the object surface while an angle of 90° has the detector face perpendicular to it. The angle influences collimator length as well as the scattered photon signal. Detector angle should not be set below 45° because at that point it is impossible for Z collimators to block signals originating from certain depths. To be more clear, the shallower angles actually invert the concept of Z collimators; they would instead block signal from a certain depth and above rather than a certain depth and below. This code was designed to only consider the latter situation and therefore would provide wrong answers or break if the detector angle was below 45°.

It's always a good idea to plot and investigate the systems design before implementing it into MCNP and collecting results.

The collimator classes are the workhorses in the system design module since they are the component that enables enhanced imaging in two dimensions at once. Without collimation, detector pixels collect scattered photons coming from too many different locations within the fan-beam and imaging would be nearly impossible due to poor resolution. By applying collimation to the detector, it's possible to block scattered photons originating from unwanted locations inside the object, allowing for better resolution and more detailed information about the points of scatter at the cost of reduced signal. The spatial discrimination in signal is useful for depth sensitive backscatter images.

A 2-D detector array has two primary forms of collimation in its collimation grid: the depth (Z) collimation and the surface (Y) collimation. Each form of collimation can be solved for independently from the other, since they influence two separate dimensions of the image. There is a unique length for both Y and Z collimators for each row of pixels in the detector array, since each row is aimed at measuring a specific depth inside the object. The fundamental relationships between system parameters and collimator length for Z and Y collimators are shown by Equations 1-1 and 1-2 below, respectively. In each case, the equations are iterated over each location (X Y, Z) of a row of pixels on the detector array (Pi) and its associated depth (d) it is trying to image. A collimator's Length is dependent on the following system parameters given by the user: height of a single detector pixel (PH); width of a single detector pixel (PW); thickness of the collimators in the grid (Ct); detector angle with respect to the object surface (θD); and the desired resolution in the y dimension (yres).

$$Length_z = \frac{P_H - C_t}{\tan(\zeta)} \quad (1\text{-}1a)$$

$$\zeta = \theta_D - \phi \quad (1\text{-}1b)$$

$$\phi = \tan^{-1}\left(\frac{P_{i,X}}{d + P_{i,Z}}\right) \quad (1\text{-}1c)$$

For Z collimators, a specific length is calculated so that its row of pixels cannot see scattered photons beyond a certain specified depth. However, since the Z collimator above the current row of pixels is being optimized for the row of pixels above it, it is not possible to specifically block photons from a specified "upper" depth. Therefore it's possible, for example, that even though a pixel row in the detector is collimated to see nothing deeper than 4 cm, it could potentially see scattered photons from any point above that depth, all depending on how long the Z collimator above it is.

$$Length_y = \frac{2L}{\frac{y_{res}}{P_W - C_t} + 1} \quad (1\text{-}2a)$$

$$L = \sqrt{\left(P_{i,X} + \frac{P_H}{2}\cos(\theta_D)\right)^2 + \left(d + P_{i,Z} - \frac{P_H}{2}\sin(\theta_D)\right)^2} \quad (1\text{-}2b)$$

The Y collimators are calculated at the center of a pixel and are as long as they have to be to insure that each pixel has a resolution of yres as specified by the user. The downside is that it's impossible for yres to equal the size of the visible pixel width (PW−Ct) because that would mean the collimator length is as long as the path length of the scattered photon (L), which is mostly inside of the object. Having a collimator penetrate the object defeats the purpose of "non-destructive" testing. Even when yres is 3-4 times the size of the pixel width, collimator lengths can be prohibitively long and greatly reduce SNR. This is an inherent drawback to backscatter systems that utilize photon sources and detectors greater than one dimension.

The first type of collimator designed for this toolkit was the optimized collimation grid, which was thought to be an advancement over the uniform collimation designs, discussed in the next section. Table 3 below describes the key attributes needed to design an optimized collimation grid.

TABLE 3

List of variables required from user for Collimator class (optimized collimation grid).

| Variable | Description (Units) |
|---|---|
| $C_1$ | Thickness of the collimators in the collimation grid (cm) |
| max depth | Maximum depth the system can see (cm) |
| $O_B$ | Offset distance of the detector array ftms the fan-beam (cm) |
| $O_S$ | Offset distance of the defector array from the object surface (cm) |
| $y_{res}$ | Resolution of the image pixels in the Y dimension (cm) |
| material | Type of material the collimator is made out of (ex: Tungsten) |

The optimized collimation grid class is simply called Collimator. This class contains attributes like max depth, collimator thickness, and offset distances from the surface and fan-beam. Max depth is the deepest point the entire system will see and is the value that the bottom row of detector pixels (closest to surface) are set to view. It also is the depth used to calculate the fan-beam collimators discussed earlier. Since the thickness of a collimator will block a portion of each detector pixel, it's important to watch this attribute in combination with pixel dimensions. Make the collimators too thick or the pixels too small and you'll entirely block signal because you essentially made a lead sheet over the detector. Offset distances provide a hard limit for how close the detector and its collimation grid can get to the fan-beam and object, since you want neither the collimator blocking the fan-beam nor scraping the object surface.

The methods contained inside Collimator take a Detector instance and uses its information to help create the correct lengths for each row of Z and Y collimators. It utilizes Equations 1-1 and 1-2 as well as others in order to place the detector/collimator system as close as possible to the surface and fan-beam while at the same time ensuring the proper resolution and viewing depths are achieved.

The material attribute aids in the MCNP input deck creation, since different materials can be used to create collimators; two of the most common being lead and tungsten.

The uniform collimation grid class, named UniformCollimator, is a simplified version of an optimized collimation grid. The attributes necessary for this class are similar to that of the Collimator class, with a few exceptions, as seen in Table 4 below. The max depth and y res attributes are no longer required, since they are no longer optimized and controlled by the user. Instead, they get calculated once the collimators have all been created with the same requested length. This kind of collimation grid design should be easier to manufacture and can sometimes create results just as good as an optimized collimation grid.

TABLE 4

List of variables required from user for UniformCollimator class (uniform collimiation grid).

| Variable | Description (Units) |
|---|---|
| $C_1$ | Thickness of the collimators in the collimation grid (cm) |
| length | Length of all the collimators in the collimation grid (cm) |
| $O_B$ | Offset distance of the detector array from the fan-beam (cm) |
| $O_S$ | Offset distance of the detector array from the object surface (cm) |
| material | Type of material the collimator is made out of (ex: Tungsten) |

The entire design process is done inside Python but it is MCNP that will actually simulate an image using that design. It would be extremely tedious to manually input the proper values in order to replicate the system inside MCNP. Therefore the MCNP module is supplied, which contains a method specifically for converting the designed system into proper MCNP format as well as some generic methods for inputting the most common cards used in MCNP such as cell cards, surface cards, tally cards, etc.

Data for the detector and collimators in the grid are stored in their classes in a style that matches the BOX Macrobody format of MCNP. Therefore all the collimators are written as such inside the input deck, while the detector is also turned into an FMESHn4 tally. Each element in the mesh tally matches the number and dimensions of the detector pixels.

Collimator cells are made of whatever material is requested by the user while the detector cell is a void, since the analysis seeks to be independent of detector composition. Properties such as detector efficiency can be applied during post processing of the results if desired. Since the FMESH tally is a measure of the photon flux over all surfaces of a volume, the detectors are made sufficiently thin so that the results will approach that of a surface current over just the face of the detector pixels and not their other sides.

The cards generated to make the system are all assigned a coordinate transformation (TR) card. This enables the easy creation of multiple input files, modeling the scanning motion of the system over an object. Only the TR cards need to be adjusted by the system step size instead of recomputing and rewriting every surface and cell card.

Both the visualize and matplotting modules provide options for viewing the designed Backscatter System. These tools are purely for qualitative purposes, such as observing the scale of the collimator lengths with respect to other system properties and checking that no errors occurred. Quantitative information about the system is stored inside the classes of the backscatter design.

The tally reader module contains a CartesianMeshTally class that is able to read meshtally output files that are generated by MCNP when FMESH tallies are used. The class compiles the tally data into arrays which can then be visualized with common tools available to Python.

To test the capabilities of the toolkit, as well as provide a trial for depth sensitive imaging using a 2-D XBI system, a former MCNP simulation was replicated from a Master's Thesis at UF. In the thesis, they briefly discuss the possibility of 2-D backscatter imaging and attempt a simple image in MCNP of an aluminum block with a ring of air embedded in it.

The MCNP simulation used in the thesis described a 2-D detector array that was 6 rows with 40 pixels each, for a total of 240 pixels in the array. Each pixel was 2.5 mm high and 1 mm wide. The detector array was angled at 45° and a 120 keV fan-beam was used. A 1.5 cm long and 0.4 mm thick tungsten collimation grid was placed over the detector. Therefore a uniform collimation grid was used. Since the offset distance of the collimators/detector from the object surface and fan-beam were not provided, a best guess was used (0.9 cm from surface and 2.55 cm from fan-beam). The X-ray fan-beam was set to 5 cm above the object surface.

The phantom being imaged was a solid block of aluminum with a ring of air placed 1 cm deep inside of it. The ring of air was 1 cm thick, had an inner diameter of 0.5 cm, and an outer diameter of 1.5 cm.

Figure 17:
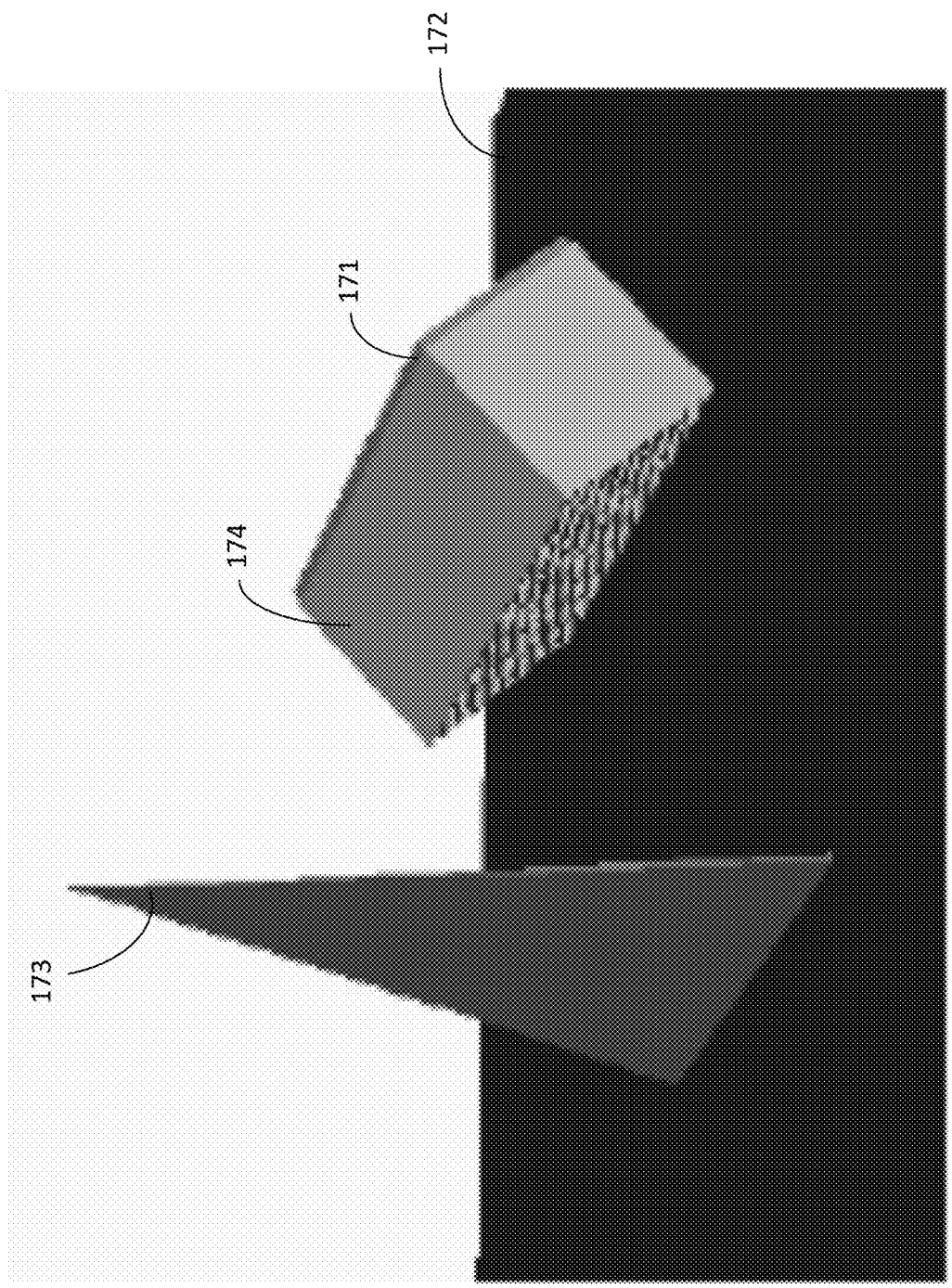
FIG. 17 shows a replicated XBI system having a detector that uses a collimation grid was designed using a toolkit and then visualized in 3-D using a visualize module.

FIG. 17 shows the replicated XBI system that was designed using the toolkit and then visualized in 3-D using the visualize module. The detector array 171 was angled at 45° relative to the surface 172 of the object 172 being imaged and a 120 keV fan-beam 173 being used as the source. As indicated above, a 1.5 cm long and 0.4 mm thick tungsten collimation grid 174 is placed over the detector array. The system was then exported to an input deck for MCNP and then the test phantom was input by hand into the deck.

Figure 18A:
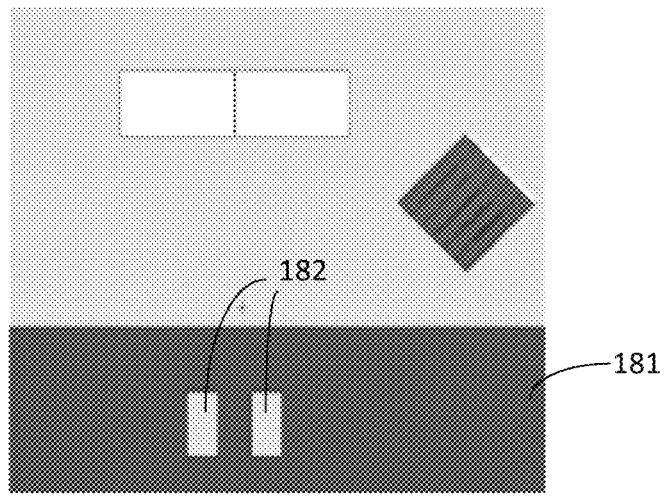
FIG. 18 shows cross-sectional views of an XBI system geometry plotted in MCNP that also shows a test phantom to demonstrate the success of the ability of a toolkit to model a 2-D XBI system and subsequently export it to an MCNP file.
Figure 18B:
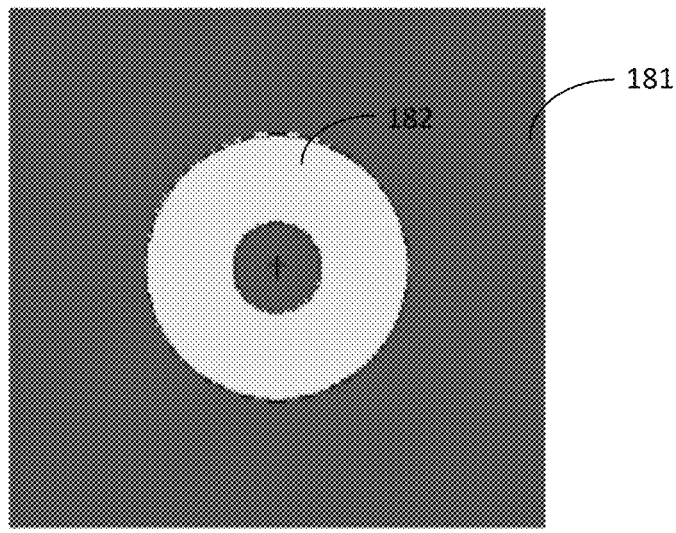
Figure 18C:
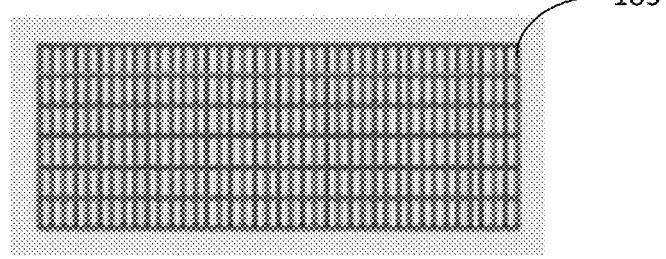

FIGS. 18A-18C show cross-sectional views of the geometry plotted in MCNP, where the test phantom and system can be seen. FIG. 18A shows the YZ plane of the model, where Z is depth into the object being scanned. The object being imaged was a uniform block of aluminum 181 with a ring of air 182 embedded in it. FIG. 18B shows the XY plane at the location of the air ring 182 inside of the aluminum block 181. FIG. 18C is captured at a plane parallel to the face of the 2-D detector array, such that the 2-D collimation grid 183 can be seen. These images show the success of the toolkit's ability to model a 2-D XBI system and subsequently export it to an MCNP file. Since MCNP simulations of a 2-D backscatter imaging system can be computationally expensive, only two scan points were simulated. The first scan point (i.e. fan-beam position) was directly over the center of the ring of air and the second point was over solid aluminum. Obtaining an image of the solid aluminum acts as a form of baseline/background signal that can be used as a filter to remove the disparities in pixel intensity due to a divergent fan-beam source and photon attenuation. When you divide your 2-D image slices by the aforementioned filter, pixels that had lower signals near the edges and bottom of the scans will be given more weight since they're being divided by smaller values in the filter (because signal was also lower in that image due to the same reasons of source divergence and attenuation). Any changes in density/material will stand out because it will have a noticeably different signal than what was in the scan of the bulk homogenous material of the filter image.

Figure 19:
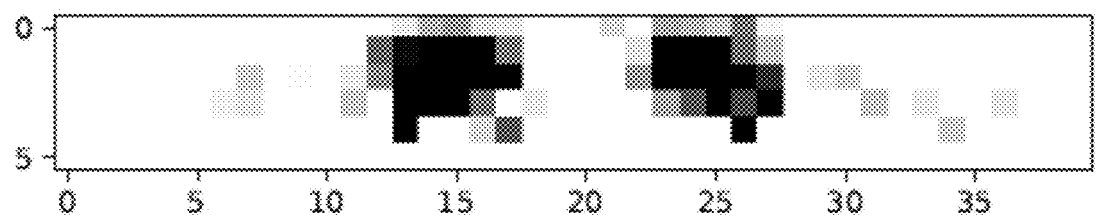
FIG. 19 shows a filtered image of the ring of air obtained by an XBI system simulated in MCNP with pixel values rescaled to help improve contrast.

FIG. 19 shows the filtered image of the ring of air, which has had its pixel values rescaled, to help improve the contrast of the air and aluminum. Each row in the image represents a row in the detector array looking at a different depth in the phantom. This figure shows that depth sensitive imaging is a possibility, since the two black regions, representing the cross-sectional view of the air ring, are located near the middle of the image. This corresponds to where the air ring was located inside the phantom.

Figure 20:
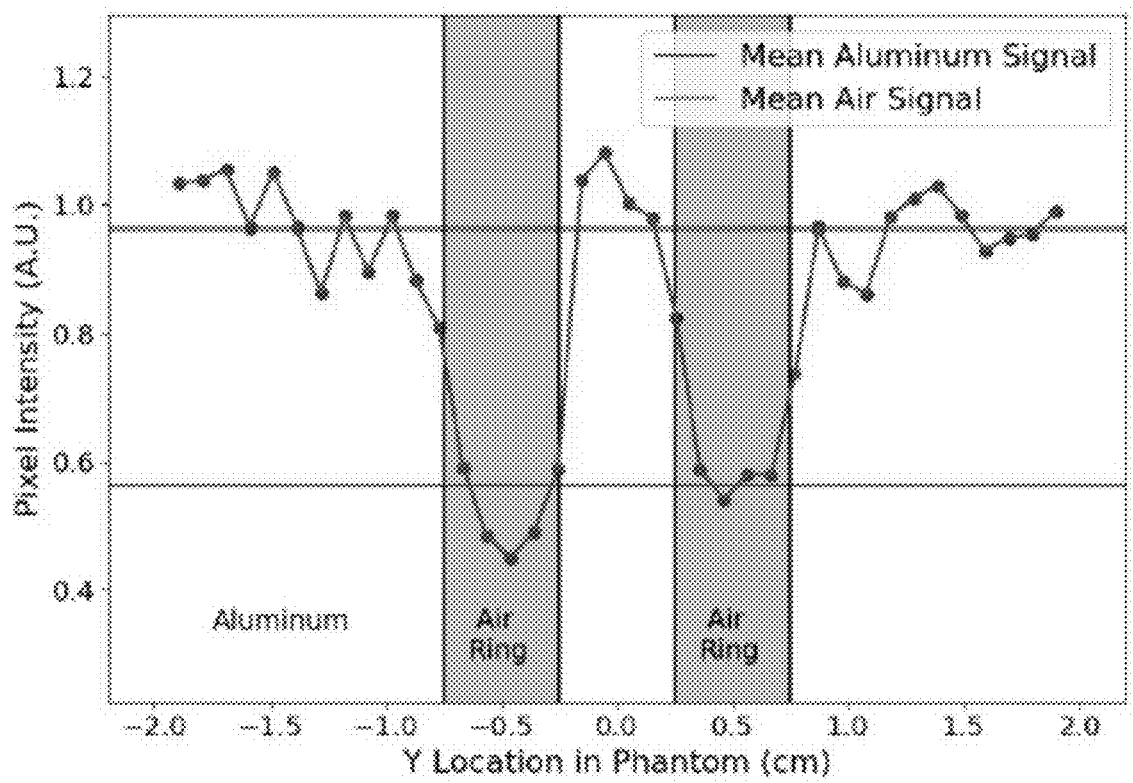
FIG. 20 shows the pixel values for the filtered image shown in FIG. 19 along the middle row of the 2-D detector array.

FIG. 20 shows the pixel values for the filtered image along the middle row of the 2-D detector array (row 2 in the Y axis of the image in FIG. 19). The physical locations of the phantom materials have been superimposed over the pixel values to help show where the contrast in signal should appear. There seems to be good agreement with the line plot of pixel values along with the physical change in density/ material inside the test phantom. It was estimated that it takes a span of roughly two pixels to shift from the aluminum signal to the air ring signal. Since the pixels in the 2-D detector array were set to have a physical width of 1 mm, this means the imaging resolution for this system is estimated to be 2 mm. This resolution is for the fan-beam dimension (Y dimension in the MCNP simulation). The resolution in the scanning dimension (X dimension in this simulation) would be determined by how thick the fan-beam was as well as the scan step of the system.

The test results described above showed that 2-D XBI systems have the potential to achieve depth-sensitive imaging. However, in accordance with the following example embodiment, instead of using energy discrimination to separate depth information, a higher dimension of detectors are used, namely, a 2-D array of pixels. Each row in the array looks at a different depth, the resolution of each depth slice is dependent on the length of the collimation used (specifically the Z collimators mentioned above). As long as the collimation grid does not become too long, then a 2-D XBI system can acquire images at a faster pace than that of a pencil-shaped beam system, at a reduced resolution. If the grid becomes too long, then too much signal is filtered out and the dwell time for each scan point becomes prohibitively long, thereby becoming no faster than a pencil-shaped beam design.

The following discussion looks at two different methods of scanning for a 2-D XBI system. The first is a simpler, linear scanning method. The system starts at one end of the object and scans across in one dimension, until it reaches the other end. If the system is scanning in the X dimension, then at each point in the scan the system is acquiring scattered signals in the Y dimension (for every column of pixels) and in the Z dimension (for every row of pixels). In the end, a 3-D array of pixel data is collected: a series of 2-D radiographs, one at each depth/row in the object/detector. The second method to be discussed later is a rotational method that uses an image reconstruction algorithm to reconstruct the image.

In order to make an accurate comparison between the two methods, the same system design and test phantom are used.

Using the Python toolkit, a 2-D XBI system with an optimized collimation grid was made. The X-Ray source that generated the fan-shaped beam was placed 25 cm above the object surface and used a 150 kVp, unfiltered, lead target spectrum, produced by Specktr. With an average energy of 57.6 keV, the photons have a mean free path of 1.50 cm in the concrete that was modeled (based on mass attenuation data from NIST). The 2-D detector array was placed at a 45° angle and was 5 rows by 56 columns. Each pixel in the array was 5.5 mm high and 5.5 mm wide, so at each scan point the detector array imaged a 2.75 cm deep by 30.8 cm wide area. The detector was made 1 mm thick. The optimized collimation grid was set to have a max depth of 6 cm and a desired y-resolution of 8.6 mm, made of tungsten collimators that are 0.5 mm thick. The detection/collimation was offset from the fan-beam by 2.7 cm and from the object surface by 1 cm. The systems step size was set to 5 mm.

The test phantom was very similar to the one used in the proof of concept study discussed above, and therefore FIGS. 10A and 10B should be referred to for a picture of the phantom in MCNP6. It was a block of solid, regular concrete, spanning 80 cm in the X and Y dimension and 20 cm deep (Z dimension). The letters U and F were still 2 cm wide, except the U was made of water and the F of 316 stainless steel. Since these materials are much more attenuating than tissue, but the X-ray energy spectrum was still 150 kVp, the letters were moved much closer to the surface. The letter U was embedded at a depth that spanned from 0.6 cm to 1.3 cm deep. This range corresponded to the depth that the second row (from the top) of detector pixels was calculated to image. The letter F was placed in the range for the next row beneath it (3rd row from top). It spanned a depth of 1.38 cm to 2.08 cm.

The system scanned the phantom in 36 steps. With 5 mm step size, this corresponds to a scan length of 18 cm. A complete scan comprised a 3-D image that was 36×56×5, with a field of view spanning 18×30.8×2.75 cm.

FIGS. 21A-21E show the resulting 3-D images acquired by a 2-D XBI system simulated in MCNP6. Each 3-D image (width, length and depth) is of a different depth/detector row. As was done with the test image, a background filter was applied to every scan point in order to remove effects of attenuation and fan-beam divergence. The image slice at the first scan point (FIG. 21E) was used since it was when the system measured a uniform concrete signal. By dividing every other scan point/row in the images, the imaging artifacts are removed and the contrast in signal from other materials is enhanced, making it easier to see. Since the changes in signal can be very subtle between materials, readjusting the pixel gray-scaling is typically needed in order to better see the features; this was done in FIGS. 21A-21E. The letter U produces a brighter signal because it scatters photons more frequently than it absorbs them with respect to the other materials present for this range of X-ray energies. The letter F still has a higher likelihood to absorb photons at these energies and therefore produces a darker signal.

With respect to the phantom, the letter U should be visible in the second image and deeper (image at 0.958 cm in FIG. 21B), while the letter F should be visible in the third image and deeper (image at 1.735 cm in FIG. 21C). The reason they will be visible for every image deeper is because the feature is affecting the primary beam path of the X-rays, so they will always influence the signal collected whether or not they are actually scattering from that feature at that measured depth. But if signal is being measured from scattered X-rays above the feature, then it will not be visible since it is not influencing any part of the beams path at that point.

To an extent, this concept holds true for FIGS. 21A-21E, except some shadows can be seen of the letters at depths above which they do not belong. There is also the problem of very poor image quality in these figures, which is believed to be caused by a few factors. First, the X-ray energy spectra is likely too weak to penetrate the phantom well and provide significant signal. Second, the optimized collimation grid that was used to achieve the desired depths and resolutions caused extremely long fins to be used; they ranged from 8-26 cm long. These exceptionally long collimators create a very small solid angle for which photons can reach the pixels, which leads to longer scan times. This is reflected in the MCNP6 simulations. After 36.5 billion particles were run, which took over a week to finish the full image, uncertainties in the meshtallies were still unacceptably high. These high uncertainties affect the image quality in FIGS. 21A-21E. Continuing to run simulations even longer until all uncertainties are sufficiently low (less than 10%) is far too time consuming to be practical. This problem seems to be inherent to fan-beam designs. Variance reduction techniques can be used to reduce this problem.

This complexity of creating real 3-D images using a 2-D XBI system comes from the fact that it is single-sided imaging. Each row in the detector that sees deeper in the object will inherently have worse resolution than the depths/ rows above, simply because the object being imaged is farther away from the detector pixels, as discussed in more detail below with reference to FIG. 22. This means those pixels seeing deeper have a larger field of view and can receive scatter signals from depths deeper and shallower than what would be desired, resulting in detecting features in an object that are located at different depths than what that row of pixels is intended to see.

The depth resolution of a 2-D XBI system is not equivalent to the resolution set for each row in the detector array, but is a few times larger, spanning multiple rows. This is an inherent drawback to single-sided imaging and requires careful attention when designing a system. It may be possible to overcome some of the resolution setbacks by using more rows and smaller pixels.

The second, rotational method mentioned above is a technique for 2-D backscatter imaging that involves rotating the system instead of linearly scanning it across an object. During a linear scan, the object is being viewed from only one direction, which can cause shadows and streaks, like what was discussed above and was visible in FIGS. 5 and 6. One way to mitigate this in linear scanning 2-D backscatter systems is to have two 2-D detector arrays, one on each side of the fan-shaped beam. Combining the signal from both sides would provide better count rates and help remove the potential streaking effects.

The idea of rotating the system instead would solve the same problem while still only needing one detector array, although a second detector array can still be added and used to either cut scan times in half or can help improve count rates by combining the signals from both detectors. By rotating the system, i.e., the X-Ray detector array and the X-Ray source around a center point, the features in an object can be imaged from different viewpoints and beam paths, creating a cleaner image with less artifacts than would be inherent in a linear scanning method.

An alternative to rotating and/or translating the system while holding the object in a fixed position is to rotate and/or translate the object while holding the system in a fixed position. Another alternative is to rotate and/or translate the object while also rotating and/or translating the system. What is important is that relative rotational and/or translational motion between the system and the object is created. For rotational motion, the detector—object need only rotate 180° if for all rotations the object is fully projected on detector plane (i.e., if object is sufficiently large then the detector area may be insufficient for complete projection image). Rotation by 360° gives more projections and potentially better image quality in reconstruction.

For fair comparison, the same system design and test phantom discussed above were used to perform the method that uses relative motion to obtain the necessary projections. The number of scan points (36) were kept the same as well as the number of particle histories for the simulations (36.5 billion). In the rotating technique, each scan point is a different angle, to a maximum of 360°. Having 36 scan points means the system is rotated in 10° increments, rather than the 5 mm steps described for the linear scan.

Since a rotating technique collects signals of the same points in an object from multiple positions, image reconstruction algorithms are needed in order to correctly map all of the data back into a common 3-D space that describes the object. The use of reconstruction algorithms is the hallmark of computed tomography (CT), which is widely used in medical imaging. However, all current methodologies are designed around transmission imaging, where full 360° access is available. If image reconstruction is to be feasible for a single-sided backscatter system, then a novel reconstruction algorithm is needed, which is disclosed herein.

Inspiration for a backscatter image reconstruction algorithm was taken from the analytical and iterative reconstruction algorithms used in single-photon emission computed tomography (SPECT). In SPECT, the objective is to measure the 3-D source distribution inside of a patient that has been administered with a gamma emitting pharmaceutical. The analogy to backscatter imaging is to measure the unknown, 3-D distribution of photon scatter intensities inside the object being irradiated. In this sense, the attenuation of the primary beam path is being ignored and each pixel in the detector array is assumed to be measuring the intensity of photons being emitted from within the object, as if photon emitters were present inside.

The approach that was designed by the inventors used the analytical method of ray-driven backprojection. The implementation of a discrete backprojection algorithm for backscatter imaging is given below by reconstruction equation 1-3:

$$\tilde{b}(x, y, z) = \sum_{k=1}^{p} g(s, z, \theta_k) w_r(x, y, z, \theta_k) \Delta\theta \quad (1\text{-}3)$$

where p is the number of projections acquired over $2\pi$ radians, $\theta_k$ is the kth angular position of the detector, and $\Delta\theta$ is the angular step between two successive projections ($\delta\theta = 2\pi/p$). The attached Appendix provides the Python computer code for performing the reconstruction algorithm in accordance with a representative embodiment. Let the imaged region of an object be thought of as a 3-D matrix of voxels M(x, y, z). The goal is to find $\tilde{b}$(x, y, z), the result of the backprojection at voxel M(x, y, z). The SignalMap class contains g(s, z, $\theta_k$), which is all of the physical data output from the detector of the XBI system at each scan step. VoxelMap keeps track of the physical dimensions M(x,y,z) and calculates the weights applied to SignalMap [$w_r$(x,y,z, $\theta_k$)]. A separate function performs the above equation to actually reconstruct the image. g(s, z, $\theta_k$) is the imaging pixel located in column $s_k$ and row z in the 2D detector array, at projection angle $\theta_k$, weighted by the path length wr (x, y, z, $\theta$k) of the ray traced through voxel M (x, y, z). The location $s_k$ is a function of the projection angle $\theta_k$ and the (x, y) coordinates of the voxel M(x, y, z):

$$s_k = x \cos\theta k + y \sin\theta k \quad (1\text{-}4)$$

The z dimension is the same for both projection images g(sk, z, $\theta$k) and voxel matrix M (x, y, z). Another way of describing Equation 1-3 is for each angle $\theta$k, using Equation 1-4, find the location sDk (on the detector) that is the projection location of point M (x, y, z). Add the value g($s_k$, z, $\theta$k), weighted by it is associated ray length wr (x, y, z, $\theta$k), to the current value of point M (x, y, z) (initial value should be 0). Repeat this process for all angles, and divide the sum by the number of projection angles.

For SPECT and other transmission tomographies, the number of projections is acquired over r radians. Projections beyond $\pi$ do not provide new information, since they are symmetric to previous projections made at angles less than n. This is not the case for backscatter, where every angle provides new information because it is rotating around a point on the same side of the object rather than rotating around the entire object.

Figure 22:
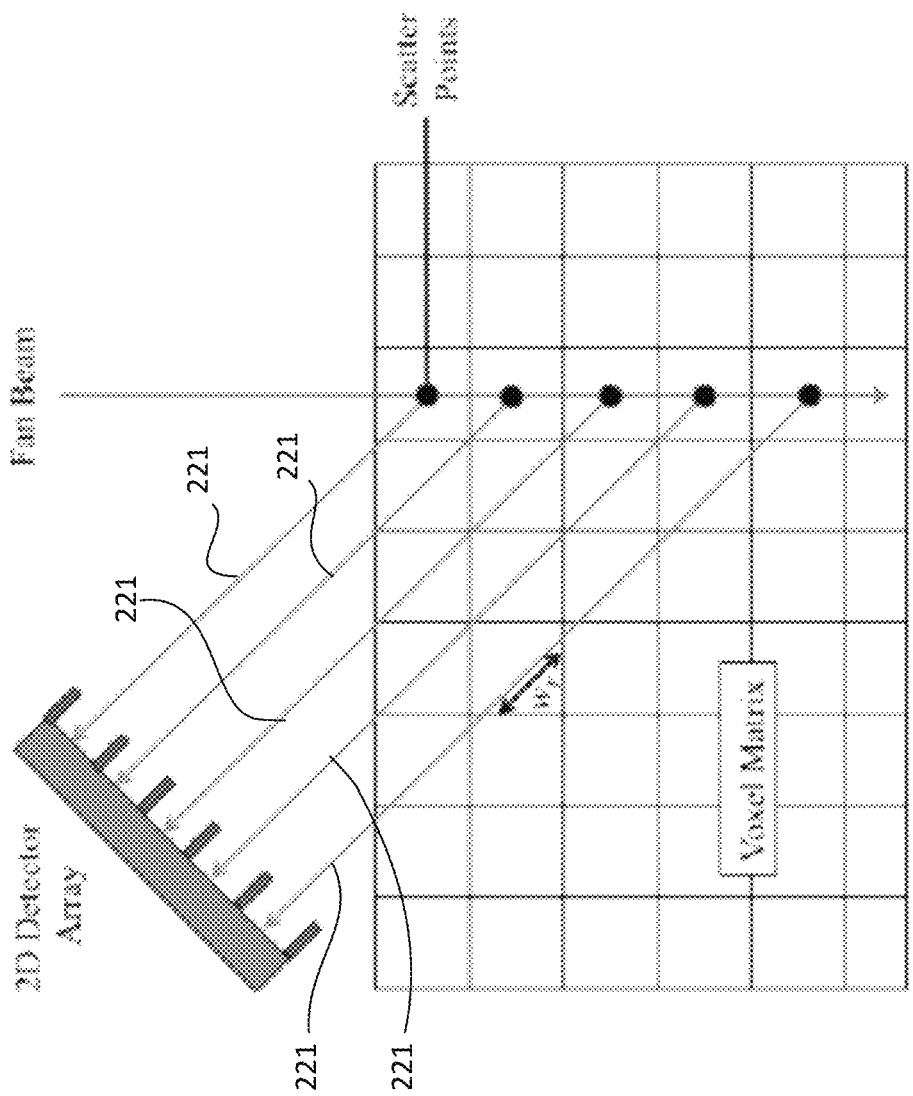
FIG. 22 shows an illustration of how rays traced from scatter points in a fan-shaped beam travel much farther distances if they are located deeper in the object.
Figure 23C:
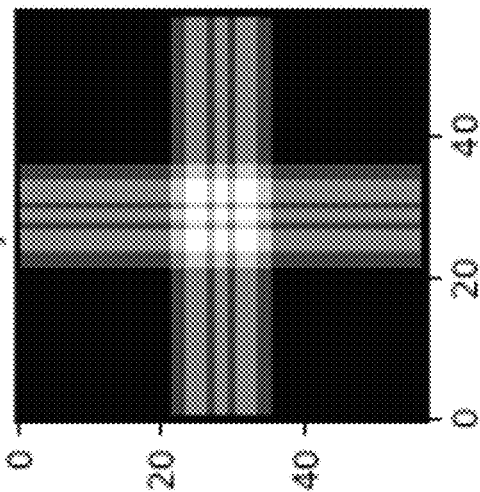
Figure 23B:
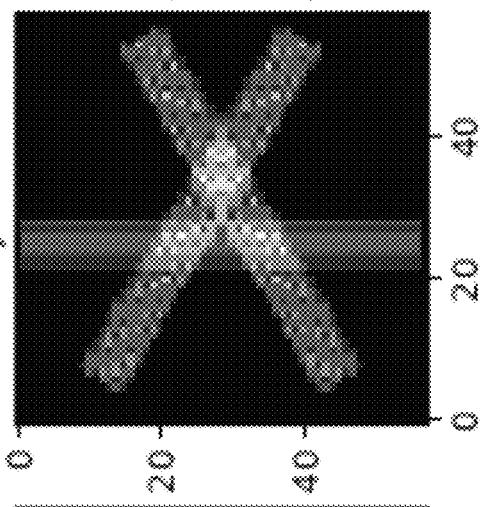
Figure 23A:
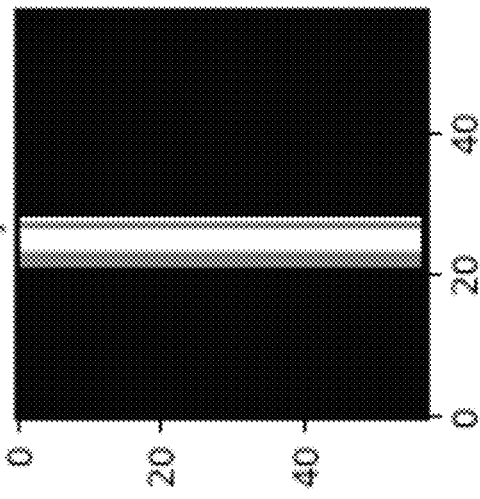
Figure 23F:
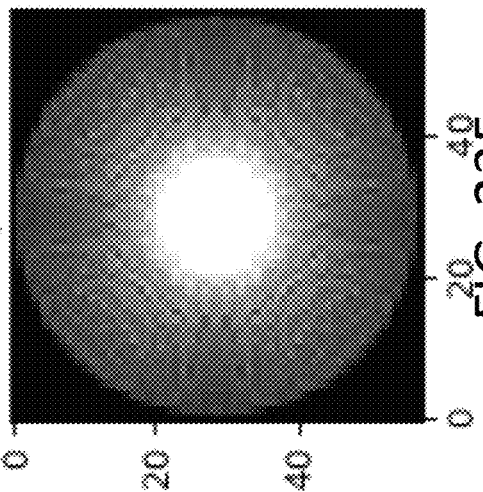
Figure 23E:
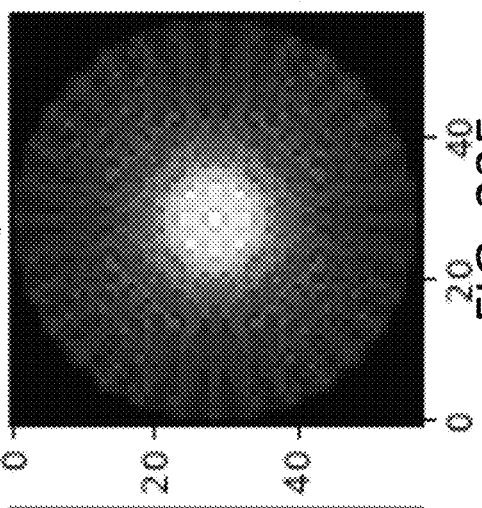
Figure 23D:
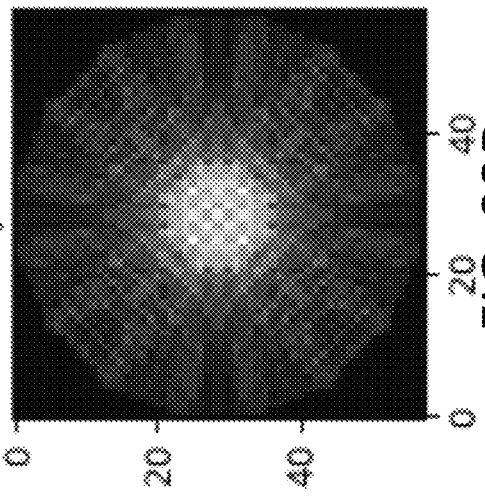
Figure 25C:
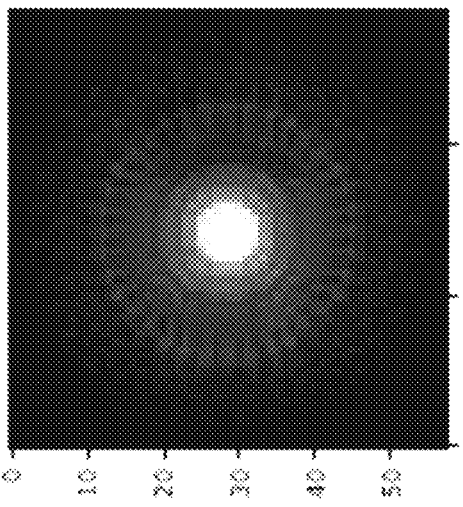
FIG. 25 shows a raw reconstructed image of a phantom acquired by a simulated rotating 2-D XBI system.
Figure 25B:
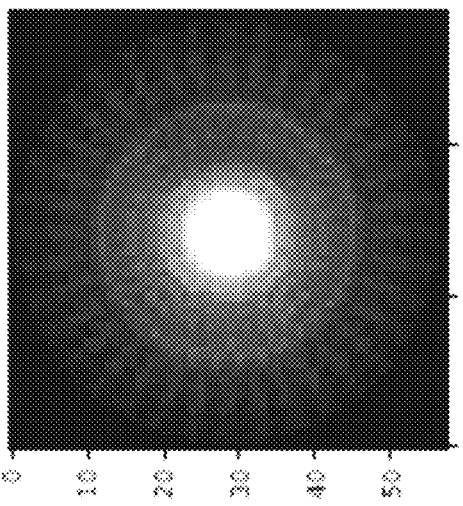
Figure 25A:
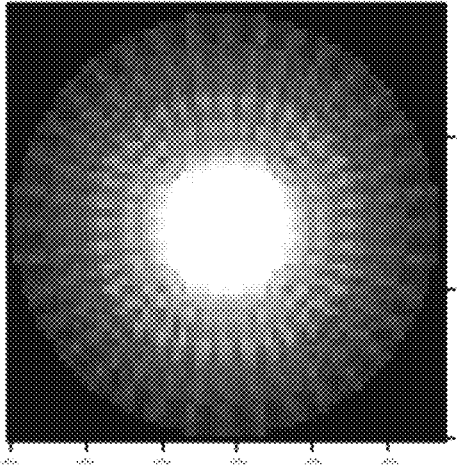
Figure 25E:
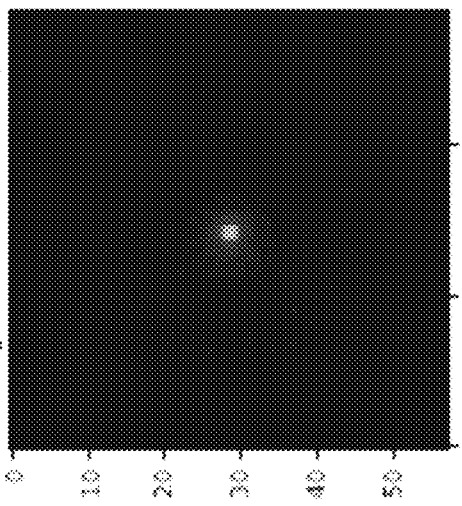
Figure 25D:
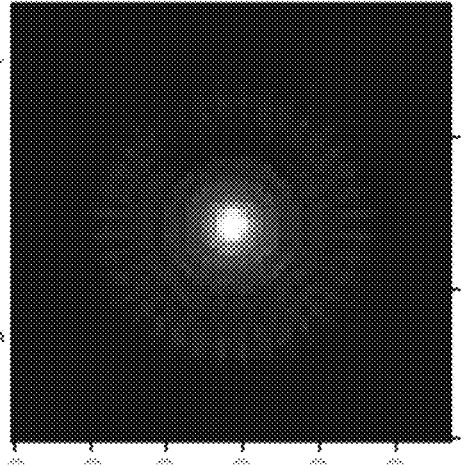
Figure 26C:
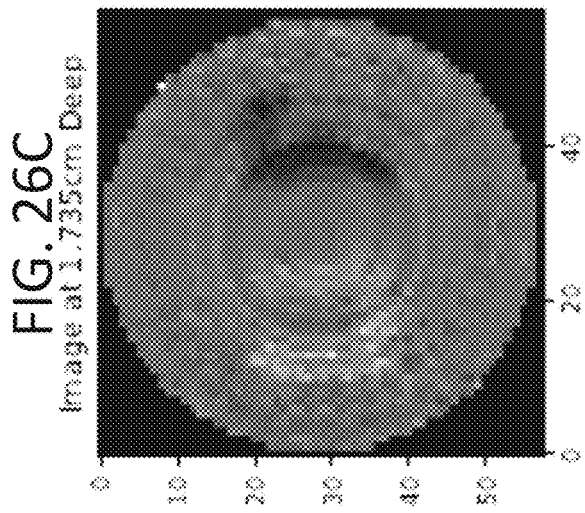
FIG. 26 shows the raw reconstructed image shown in FIG. 25 after it was filtered by dividing it by the baseline image developed from pure concrete.
Figure 26B:
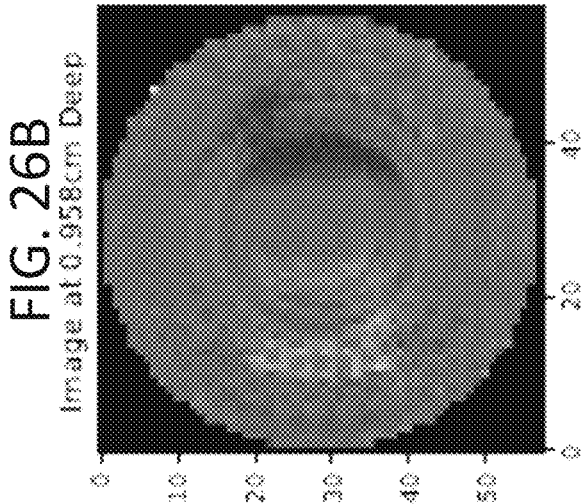
Figure 26E:
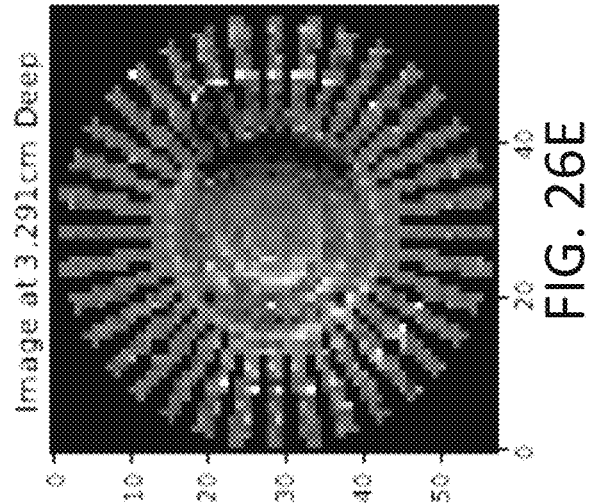
Figure 26A:
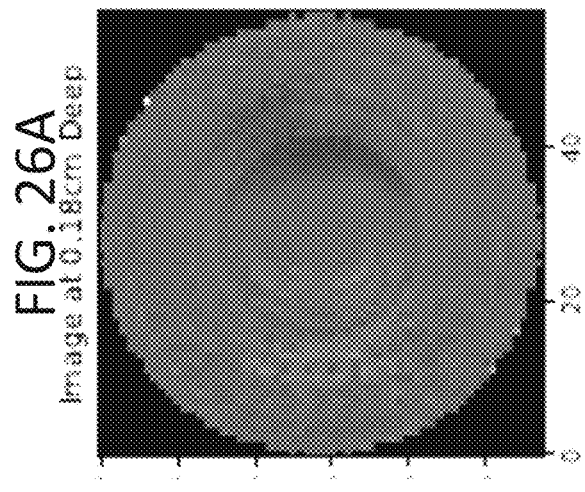
Figure 26D:
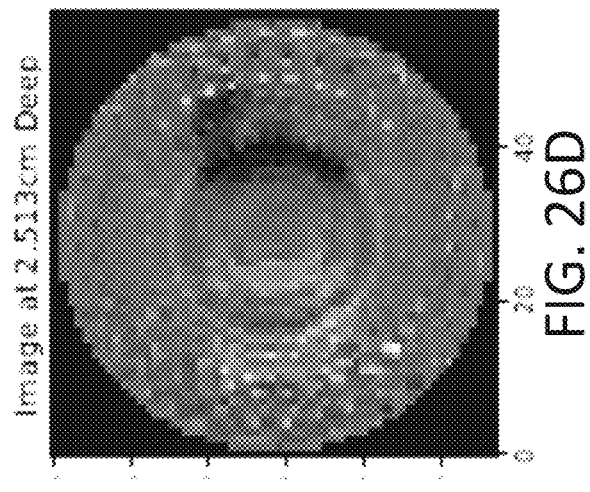

An issue that arises from images by rotating a 2-D detector array around a fixed axis on one side is the disparity of signal contribution to voxels farther away from the rotation axis and deeper within the object. FIG. 22 shows an illustration of how rays 221 traced from the respective scatter points in a fan-shaped beam travel much farther distances if they are located deeper in the object. This triangular shape of traced voxels means there is more sampling of voxels closer to the surface than at the bottom. Likewise, in the other dimension, voxels closer to the axis of rotation are sampled more than ones on the edge of the fan-shaped beam. This uneven distribution of sampling is illustrated by FIGS. 23A-23F and 24A-24F for different numbers of projections, for the top/surface of the voxel map and the bottom/deepest of the voxel map, respectively. As more projection angles are added, more information is obtained and a better image can be formed. However, the information contained in these reconstructed images will always degrade the deeper and farther away it is from the axis of rotation. Furthermore, disparities in detector signal also occur in each projection image due to the divergent fan-shaped beam source and photon attenuation in the medium.

In order to mitigate all these sources of image artifacts, a very similar approach that was discussed above is taken in accordance with an embodiment. For a linear scan, one scan of a bulk homogenous material was taken and used as a form of filter. When the scanned image slices are divided by the aforementioned filter, the effects of a divergent fan-shaped beam source and photon attenuation are mitigated. Pixels that had lower signals near the edges and bottom of the scans will be given more weight since they are being divided by smaller values in the filter (because signal was also lower in that image due to the same reasons of source divergence and attenuation). Any changes in density/material will stand out because it will have a noticeably different signal than what was in the scan of the bulk homogenous material of the filter image. This same procedure may be used for the rotational scan. All that is needed is one projection of a bulk homogenous material. One can then feed that projection to the reconstruction algorithm and it will construct an image as if the system rotated/scanned over a homogenous object. This image now contains those same artifacts due to fan-beam source divergence, attenuation, and the un-symmetric sampling from the reconstruction algorithm. This now can be used as a 3-D filter just like the 2-D one used in the linear scanning. By diving any reconstructed image by this 3-D filter, all of the artifacts mentioned will be smoothed out and result in a much more balanced image. The division is simply taking every voxel in the 3-D image and dividing it by the same corresponding voxel in the filter.

The reconstruct module inside the bacscatter2D Python toolkit, described above, was developed to handle the collection, reconstruction, and viewing of projection angles acquired during a rotational scan. Two main classes describe this module: SignalMap and VoxelMap.

The MCNP simulations are created and set up using the methods provided in the backscatter2D toolkit. In this scenario it is easier to leave the system stationary and instead rotate the phantom geometry inside the input file. Once all of the MCNP simulations have produced their meshtally data for each scanning angle, they are collected and placed in a folder, with each meshtally file being relabeled to reflect the angle at which it was taken. The SignalMap class is essentially a container that organizes all of the projection data. Given the path to the aforementioned meshtally folder, it will read each meshtally data file and store it into a dictionary (called "map"), with its key value being the angle at which the projection was taken.

The VoxelMap class is what develops the framework that allows for image reconstruction. It creates the size and dimensions of the voxel map that is to be reconstructed, namely, the voxel matrix M (x, y, z) defined earlier. VoxelMap contains the ray tracing algorithm needed for weighting the signals in each voxel. To create a VoxelMap instance, it is passed an instance of the BackscatterSystem that describes the XBI system used to take the projection images. It is also passed either an integer describing the desired number of angles to ray trace, or a SignalMap instance which contains a list of angles that the meshtallies were taken at (recommended approach).

With the information about the system dimensions and number of angles being imaged, VoxelMap steps through the ray tracing process. It stores all of the information in a dictionary called "map." The keys for this dictionary are the projection angles, identical to that of the "map" dictionary in SignalMap. The values for each key is another dictionary. In this sub-dictionary, the key is a tuple describing the column and row location of a pixel in the 2-D detector array of the backscatter system. The value for these keys are a list of voxels that the ray has passed through on its way from the scatter location within the object to its associated detector pixel. Each voxel in the list is a Voxel class containing the following attributes: x,y,z index of the voxel with respect to the voxel matrix M (x, y, z) and the path length of the ray that was traced through it. The process for this map creation is as follows:

Based on detector dimensions and maximum distance traveled by scattered photons, determine maximum dimensions of the voxel matrix M(x, y, z).

For an angle ($\theta_k$) in the list of projection angles:
transform the radial distance ($s_k$) of the detector column location into x and y coordinates in the M (x, y, z) reference frame. Detector row location is already in z coordinate.

For every x, y, z location of a scatter point in the voxel matrix M(x, y, z), trace the ray towards the associated detector pixel that images that scatter point: record the coordinates and path lengths of the voxels being traversed by the ray.

A separate method inside reconstruct takes the created SignalMap and VoxelMap and turns them into the final $\bar{b}$(x, y, z) matrix, which is the resulting reconstructed image. Since the system is rotating around a fixed point, the final image is in a cylindrical shape but it is mapped to a 3-D Cartesian space. This results in a lot of empty space (0 values) around the edges of the matrix, as can be seen in FIGS. 23 and 24. They are to be ignored and do not provide any information about the object that was imaged.

The 2-D XBI system was rotated around the center of the industrial phantom in 10° increments, for a total of 36 scan points. This was the same number of scan points used in the linear scanning method. Besides the normal scan, a separate image was reconstructed based on a solid concrete block. Since the block is uniform from all angles, only a single scan point is needed. The single scan is repeatedly stored in the SignalMap at the same angular positions as the actual scan of the true phantom. This enables the creation of a baseline image that can be used to filter the actual image and remove any reconstruction artifacts that occur.

FIGS. 25A-25E show the raw images of the phantom after it has been reconstructed for different depths inside of the phantom. FIGS. 26A-26E show the same images as in FIGS. 25A-25E after they were divided by the baseline image filter developed from pure concrete. The original, raw images are heavily obscured by the scan's over sampling near the center of the image, making it difficult to see anything. Once the image is filtered by the baseline concrete image filter, however, the images become more uniform and the letters U and F become much more visible.

Figure 27:
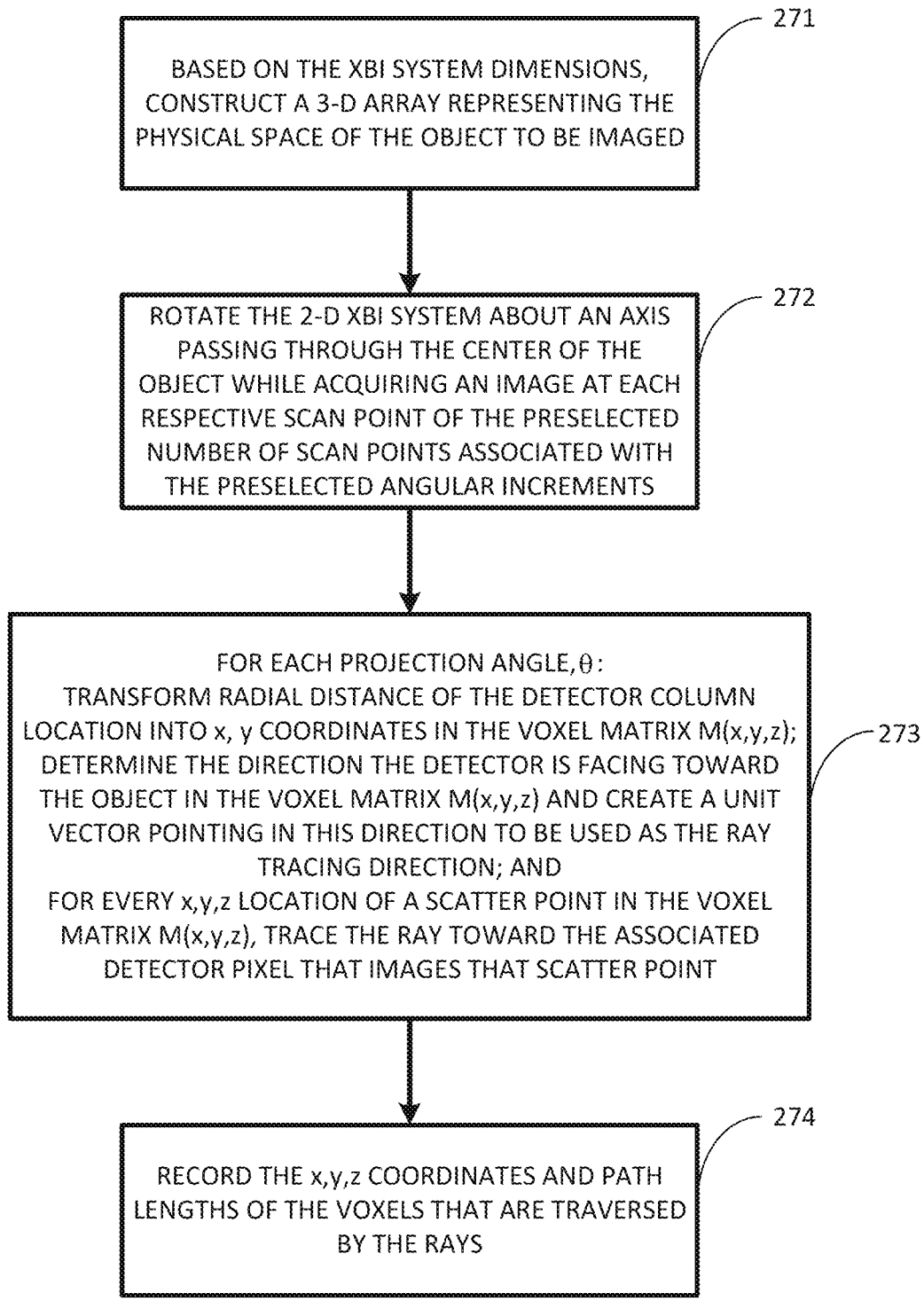
FIG. 27 is a flow diagram representing image acquisition using the 2-D XBI system and reconstruction by performing the reconstruction algorithm described above to reconstruct a 3-D image in accordance with a representative embodiment.

FIG. 27 is a flow diagram representing image acquisition using the 2-D XBI system and backscatter reconstruction using the reconstruction algorithm described above to reconstruct a 3-D image in accordance with a representative embodiment. As indicated above, the Python computer code that was written for performing the reconstruction algorithm in accordance with this representative embodiment is contained in the attached Appendix. The computer code contained in the Appendix is an example of the manner in which the reconstruction algorithm can be implemented, and the inventive principles and concepts are not limited to the implementation example contained in the Appendix, as will be understood by those of skill in the art in view of the description provided herein.

Prior to performing image acquisition and reconstruction, the VoxelMap class is generated. As indicated above, the VoxelMap class contains a 3-D array that represents the physical space intended to be imaged in the object. This 3-D array is the aforementioned voxel matrix M(x,y,z). Subsequently during reconstruction, the reconstruction algorithm adds/modifies the values inside of this 3-D array. The scale of the dimensions of this 3-D array are entirely determined by the properties of the XBI system (x-ray fan beam dimensions, detector dimensions, how many angles are being scanned). Therefore, this class is passed the XBI system properties/dimensions as well as the desired number of scanning steps in order to build the 3-D array and understand the physical dimensions of this array. The VoxelMap class keeps track of the physical dimensions M(x,y,z) and calculates the weights to be applied to SignalMap [$w_r$(x, y, z, $\theta_k$)] during the subsequent reconstruction process. Block 271 in FIG. 27 represents the process of constructing this 3-D array.

During image acquisition, the 2-D XBI system is rotated around an axis passing through the center of the object in preselected angular increments (e.g., 10° increments) for a preselected number of scan points (e.g., 36), with an image being acquired at each scan point, as indicated by block 272. As discussed above, the SignalMap class contains a dictionary that associates each image acquired by the detector with each respective scan point and each corresponding angle at which it was acquired. Each image acquired is a 2-D array: one dimension spans the breadth of the surface of the object while the other dimension is the depth of the object that the detector sees. The scale of the dimensions is entirely determined by the properties of the detector (pixel width/height, collimator lengths surrounding pixels, number of pixels in detector array). There are as many data points in the 2-D array as there are pixels in the 2-D detector array. The SignalMap class contains g (s, z, $\theta_k$) of equation 1-3 above, which is all the physical data output from the detector at each scan step.

Block 273 represents the reconstruction process. For each projection angle $\theta_k$ in the list of projection angles:
(1) the radial distance ($s_k$) of the detector column location is transformed into x and y coordinates in the reference frame of the voxel matrix M(x, y, z); the detector row location is already in z coordinate; and
(2) for every x, y, z location of a scatter point in the voxel matrix M(x, y, z), the ray is traced towards the associated detector pixel that images that scatter point.
The coordinates and path lengths of the voxels being traversed by each ray are recorded, as indicated by block 274.

Figure 28:
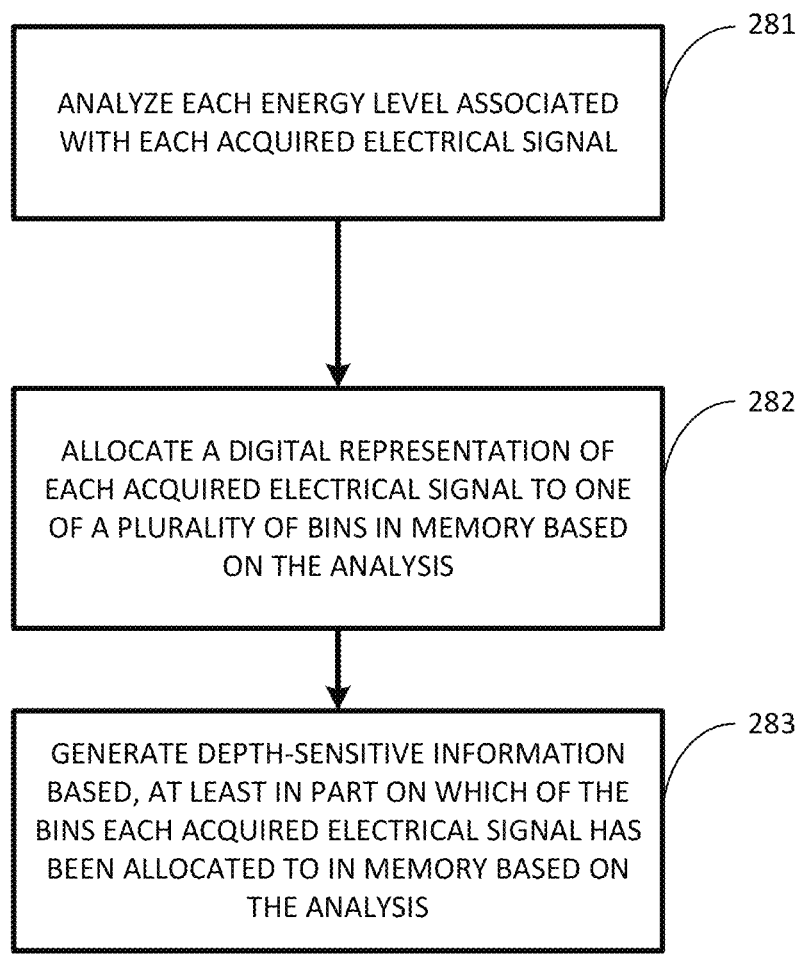
FIG. 28 is a flow diagram that represents the binning algorithm discussed above with reference to FIG. 1 in accordance with a representative embodiment.

FIG. 28 is a flow diagram that represents the binning algorithm discussed above with reference to FIG. 1 in accordance with a representative embodiment. In accordance with this embodiment, each respective energy level of each of the acquired electrical signals is analyzed to determine whether it is above or below a TH value or within a particular energy interval, as indicated by block 281. In some cases, depth-sensitive information can be obtained based on a determination of whether the energy levels exceed a TH value. In other cases, depth-sensitive information can be obtained based on a determination of whether the energy levels is below a TH value. In other cases, depth-sensitive information can be obtained based on a determination of whether the energy levels is within a particular energy interval. Block 281 represents all of these different determinations. Block 282 represents allocating a digital representation of each respective acquired electrical signal to one of a plurality of bins in memory based on the results of the analysis of block 281. Depth-sensitive information is then generated based, at least in part, on which of the bins each of the acquired electrical signals has been allocated to in memory, as indicated by block 283.

Summary and Conclusions

Compton scatter imaging is a technique similar to that of transmission radiography except that it utilizes the inelastic scattering of photons to acquire spatial information about the object under investigation. X-ray backscatter imaging can be considered a subset of CSI, where X-rays are the photon source and the detectors are placed on the same side as the X-ray source. The ability to image the internal structure of objects while only needing access to one side has useful applications in non-destructive testing and the potential for use in medical imaging. Situations that XBI excels at are when the object being imaged is either too voluminous or access to its opposite side is impossible/impractical.

X-ray backscatter designs typically acquire only 2-D images and previous attempts to go beyond that involved multiple scans. In accordance with the inventive principles and concepts, two new techniques are provided for imaging tomosynthesis using X-ray XBI systems.

The first technique uses energy discrimination in the detectors. By binning the signals collected into different energy groups, depth-sensitive information is obtained about the object, since the energy of an X-ray affects the depth at which they are most likely to scatter. The second technique uses fan-shaped beam geometries and collimated 2-D detector arrays, which was referred to above as the 2-D XBI system. Through proper calculation and design, the pixels in the 2-D detector array can be collimated so that they see specific depths inside the object being scanned. Both linear scanning and rotational scanning, with the aid of reconstruction algorithms, were used to acquire depth-sensitive images.

It should be noted that the inventive principles and concepts have been described herein with reference to a few representative embodiments, experiments and computer simulations. It will be understood by those skilled in the art in view of the description provided herein that the inventive principles and concepts are not limited to these embodiments or examples. Many modifications may be made to the systems and methods described herein within the scope of the invention, as will be understood by those of skill in the art.

What is claimed is:

1. An X-ray backscatter imaging (XBI) system for performing tomography, the XBI system comprising:
    an X-ray source configured to emit X-rays toward an object, the X-ray source being positioned above a first side of the object;
    an X-ray detector array comprising an array of X-Ray detectors configured to detect X-ray photons backscattered from the object, the X-Ray detector array being positioned above the first side of the object; and
    image acquisition circuitry configured to acquire electrical signals output by respective X-ray detectors of the array of X-Ray detectors during a single scan of the XBI system and to generate at least one of a two-dimensional (2-D) and a three-dimensional (3-D) tomographic image of the object, at least one of the dimensions corresponding to depth-sensitive information, wherein the image acquisition circuitry comprises:
        memory; and
        processing logic, the processing logic being configured to perform a binning algorithm, wherein the binning algorithm uses N energy levels as N threshold (TH) values, respectively, and compares a respective energy level of each of the acquired electrical signals to the N TH values to determine which of N+1 bins in the memory the respective acquired electrical signal is to be allocated to, where N is a positive integer that is greater than or equal to one, and wherein the processing logic generates the depth-sensitive information based, at least in part, on which of the bins the acquired electrical signals have been allocated to in the memory.

2. The XBI system of claim 1, wherein the X-Ray source generates a generally pencil-shaped beam of X-Ray radiation and wherein the X-Ray detector array comprises a single X-Ray detector.

3. The XBI system of claim 2, wherein the single X-Ray detector is a collimated X-Ray detector.

4. The XBI system of claim 1, wherein the X-Ray source generates a generally fan-shaped beam of X-Ray radiation and wherein the X-Ray detector array comprises a 2-D array of collimated X-Ray detectors.

5. The XBI system of claim 1, wherein the X-Ray source generates a line array of generally pencil-shaped beams of X-Ray radiation and wherein the X-Ray detector array comprises a 2-D array of collimated X-Ray detectors.

6. The XBI system of claim 1, wherein the X-Ray detector array comprises an array of X rows of the X-Ray detectors and Y columns of the X-Ray detectors, where X and Y are integers that are greater than or equal to 2, the X rows and Y columns being parallel to X- and Y-axes, respectively, of an X, Y, Z Cartesian coordinate system, each of the X rows of the X-Ray detectors pointing toward a different depth in the object, the depth in the object being parallel to a Z-axis of the X, Y, Z Cartesian coordinate system, each of the X-Ray detectors being collimated, and wherein the depth-sensitive information is generated based on where each row of X-Ray detectors in the X-Ray detector array is pointed at inside of the object.

7. The XBI system of claim 6, wherein the X-Ray source generates a generally fan-shaped beam of X-Ray radiation and wherein the array of X-Ray detectors is offset from the generally fan-shaped beam and angled such that a front face of the array of X-Ray detectors is pointing toward the first side of the object.

8. The XBI system of claim 6, wherein the X-Ray source and the array of X-Ray detectors are rotated together relative to a fixed point on the object as the object remains stationary to perform the single scan of the XBI system.

9. The XBI system of claim 8, wherein the image acquisition circuitry includes processing logic that performs a reconstruction algorithm that processes the electrical signals output from the X-Ray detectors at different angles of the rotating X-Ray source and array of X-Ray detectors to reconstruct a 3-D tomographic image of the object.

10. The XBI system of claim 6, wherein the X-Ray source and the array of X-Ray detectors are in fixed locations as the object is rotated to perform the single scan of the XBI system.

11. The XBI system of claim 10, wherein the image acquisition circuitry includes processing logic that performs a reconstruction algorithm that processes the electrical signals output from the X-Ray detectors at different angles of the rotating object to reconstruct a 3-D tomographic image of the object.

12. The XBI system of claim 6, wherein the X-Ray source generates a line array of generally pencil-shaped beams of X-Ray radiation that are activated in sequence and wherein the array of X-Ray detectors is offset from the line array of generally pencil-shaped beams and angled such that a front face of the array of X-Ray detectors is pointing toward the first side of the object.

13. The XBI system of claim 12, wherein the X-Ray source and the array of X-Ray detectors are rotated together relative to a fixed point on the object as the object remains stationary to perform the single scan of the XBI system.

14. The XBI system of claim 13, wherein the image acquisition circuitry includes processing logic that performs a reconstruction algorithm that processes the electrical signals output from the X-Ray detectors at different angles of the rotating X-Ray source and array of X-Ray detectors to reconstruct a 3-D tomographic image of the object.

15. The XBI system of claim 12, wherein the X-Ray source and the array of X-Ray detectors are in fixed locations as the object is rotated to perform the single scan of the XBI system.

16. The XBI system of claim 15, wherein the image acquisition circuitry includes processing logic that performs a reconstruction algorithm that processes the electrical signals out from the X-Ray detectors at different angles of the rotating object to reconstruct a 3-D tomographic image of the object.

17. The XBI system of claim 6, wherein the X-Ray detectors are collimated by a collimation grid that is secured to a front face of the array of X-ray detectors, the collimation grid comprising fins of high atomic number.

18. A method for performing X-Ray tomography with an X-ray backscatter imaging (XBI) system, the method comprising:
with an X-ray source positioned above a first side of an object, emitting X-rays toward the object;
with an X-ray detector array positioned above the first side of the object and comprising an array of X-Ray detectors, detecting X-ray photons backscattered from the object;
with image acquisition circuitry, acquiring electrical signals output by respective X-ray detectors of the array of X-Ray detectors during a single scan of the XBI system and generating at least one of a two-dimensional (2-D) and a three-dimensional (3-D) tomographic image of the object, at least one of the dimensions corresponding to depth-sensitive information, wherein the image acquisition circuitry comprises processing logic and memory, the method further comprising:
in the processing logic, performing a binning algorithm comprising:
analyzing a respective energy level of each of the acquired electrical signals and allocating the respective acquired electrical signal to one of a plurality of bins in the memory based on results of the analysis; and
generating depth-sensitive information based, at least in part, on which of the bins each of the acquired electrical signals has been allocated to the memory.

19. The method of claim 18, wherein the binning algorithm uses N energy levels as N threshold (TH) values, respectively, and compares the respective energy level of each of the acquired electrical signals to the N TH values to determine which of N+1 bins in the memory the respective acquired electrical signal is to be allocated to, where N is a positive integer that is greater than or equal to one, and wherein the processing logic generates the depth-sensitive information based, at least in part, on which of the bins the acquired electrical signals have been allocated to in the memory.

20. The method of claim 18, wherein the X-Ray source and the array of X-Ray detectors are rotated together relative to a fixed point on the object as the object remains stationary to perform the single scan of the XBI system or the X-Ray source and the array of X-Ray detectors are in fixed locations as the object is rotated to perform the single scan of the XBI system.

* * * * *